(12) United States Patent
Balde et al.

(10) Patent No.: US 12,139,046 B2
(45) Date of Patent: Nov. 12, 2024

(54) VEHICLE SEAT WITH MONITORING SYSTEM

(71) Applicant: FAURECIA Sièges d'Automobile, Nanterre (FR)

(72) Inventors: Mamadou Saliou Balde, Morigny-Champigny (SE); Samuel Baudu, Boulogne Billancourt (FR); Laurent Chabert, Cerny (FR); Stéphane Le Roux, Lardy (FR)

(73) Assignee: FAURECIA Sièges d'Automobile, Nanterre (FR)

( * ) Notice: Subject to any disclaimer, the term of this patent is extended or adjusted under 35 U.S.C. 154(b) by 857 days.

(21) Appl. No.: 17/149,009

(22) Filed: Jan. 14, 2021

(65) Prior Publication Data

US 2021/0213853 A1    Jul. 15, 2021

(30) Foreign Application Priority Data

Jan. 15, 2020  (FR) ..................................... 2000381

(51) Int. Cl.
*B60N 2/00* (2006.01)
*A61B 5/00* (2006.01)
*B60R 21/015* (2006.01)

(52) U.S. Cl.
CPC ............ *B60N 2/002* (2013.01); *A61B 5/4824* (2013.01); *B60R 21/01516* (2014.10); *B60R 21/01532* (2014.10); *A61B 2560/0406* (2013.01); *A61B 2562/16* (2013.01)

(58) Field of Classification Search
CPC ........ B60R 21/01516; B60R 21/01532; B60R 21/01512; B60R 21/0153; B60N 2/002; A61B 5/4824; A61B 2560/0406; A61B 2562/16
See application file for complete search history.

(56) References Cited

U.S. PATENT DOCUMENTS

| | | | |
|---|---|---|---|
| 5,890,085 A | 3/1999 | Corrado | |
| 6,366,200 B1 | 4/2002 | Aoki | |
| 7,245,956 B2 * | 7/2007 | Matthews | A61B 5/282 600/382 |
| 2001/0019272 A1 * | 9/2001 | Eisenmann | B60N 2/002 324/674 |
| 2002/0021215 A1 | 2/2002 | Pajon | |
| 2006/0033507 A1 | 2/2006 | Gaumel | |
| 2011/0029203 A1 * | 2/2011 | Watson | B60R 21/01532 701/45 |
| 2019/0193591 A1 * | 6/2019 | Migneco | G06V 40/20 |

FOREIGN PATENT DOCUMENTS

| | | | | |
|---|---|---|---|---|
| DE | 102016219165 A1 | | 4/2018 | |
| EP | 1666859 A1 * | | 6/2006 | ............. G01L 1/205 |
| FR | 2813054 A1 | | 2/2002 | |
| FR | 2849918 A1 | | 7/2004 | |
| RO | 132627 A0 * | | 6/2018 | |
| WO | 2011104399 A1 | | 9/2011 | |
| WO | WO-2017054461 A1 * | | 4/2017 | ........... B60R 19/483 |
| WO | WO-2018077646 A1 * | | 5/2018 | ......... G01N 15/0606 |

* cited by examiner

*Primary Examiner* — Milton Nelson, Jr.
(74) *Attorney, Agent, or Firm* — Barnes & Thornburg LLP

(57) ABSTRACT

A seat comprising a backrest; a seating portion connected to the backrest; and at least one measurement area defined on the backrest and/or on the seating portion, the at least one measurement area comprising at least one interdigital capacitive sensor capable of measuring a distance or a movement of a user occupying the seat.

10 Claims, 13 Drawing Sheets

VEHICLE SEAT WITH MONITORING SYSTEM

PRIORITY CLAIM

This application claims priority to French Patent Application No. FR2000381, filed Jan. 15, 2020, which is expressly incorporated by reference herein.

BACKGROUND

The present disclosure relates the field of monitoring a user who is occupying a seat. In particular, the present relates to a vehicle seat and to a measurement system provided for this purpose.

SUMMARY

According to the present disclosure, a seat comprising a backrest, a seating portion connected to the backrest and at least one measurement area defined on the backrest and/or on the seating portion. The at least one measurement area comprising at least one interdigital capacitive sensor capable of measuring a distance or a movement of a user occupying the seat.

In illustrative embodiments, this makes it possible to provide a device capable of making anthropometric measurements of a user occupying the seat, which have the advantage of being more ergonomic than comparative measurements.

In illustrative embodiments, anthropometric measurements are measurements of dimensional features of an individual, including height, chest height, lengths of limbs such as arms and legs, the person's mass or the mass of the limbs, or the corresponding centers of gravity. It is thus possible to define one or more user classifications, for example according to their gender, or according to their weight in order to distinguish a child from an adult by whether the mass of the user is greater than 25 kilograms or less than 70 kilograms, for example.

In illustrative embodiments, an interdigital capacitive sensor is a sensor comprising at least one electrode which allows detecting a variation in distance, this distance possibly being very small, based on the capacitive effect. By virtue of this capacitive effect, a determination of the distance is obtained by measuring the capacitance of the capacitor, this capacitance being inversely proportional to the distance to be measured and proportional to the product of the surface area of the sensor electrode and the permittivity of the dielectric existing between the sensor and the part to be measured. As a result, there is a direct relation between the value of a measured capacitance and the value of a corresponding distance or movement.

In illustrative embodiments, a measurement area is a surface area of the backrest and/or of the seating portion, or more generally of the seat, inside of which at least one interdigital capacitive sensor has sufficient sensitivity to detect a variation of the distance or of the movement.

In illustrative embodiments, an interdigital sensor, and in particular an interdigital capacitive sensor, is a sensor formed of at least one plate or of at least one metal electrode arranged in the shape of a comb, and preferably having two faces opposite to each other.

In illustrative embodiments, an interdigital capacitive sensor makes it possible to provide a sensor of reduced volume but which has a maximized useful surface area, which increases the capacitance and sensitivity of the sensor while reducing its thickness.

In illustrative embodiments, an interdigital capacitive sensor also allows obtaining measurements over short time intervals of about a microsecond. This makes it possible to provide a fast, precise system with high plausibility.

In illustrative embodiments, the at least one measurement area further comprises at least one resistive electrode capable of measuring a contact pressure of a user occupying the seat.

In illustrative embodiments, this makes it possible to provide a multiphysical single-technology device for monitoring the weight and/or the contact force exerted by a user on a surface of the seat, in particular the seating portion and/or the backrest of the seat.

In illustrative embodiments, the combination of at least one interdigital capacitive sensor with at least one resistive electrode makes it possible to achieve optimum sensitivity for detecting a user and/or classifying a type of user occupying the seat. This combination also allows increasing the plausibility and reliability of the data in a manner that is greatly superior in terms of their possible redundancy.

In illustrative embodiments, the use of two such different types of sensors also allows strengthening the on-board diagnostic capabilities of a vehicle, known as OBD capabilities, and the plausibility of the measurements, by using their complementarity as well as their redundancy.

In illustrative embodiments, a resistive electrode is any type of resistive sensor capable of measuring a pressure in the at least one measurement area of the seating portion and/or of the backrest of the seat, for example based on a variation in the resistivity of this element.

In illustrative embodiments, "$g/cm^2$" indicates the unit of measurement for pressure expressed in grams per square centimeter, and such that 1 $g/cm^2$ is equal to 98.0665 Pa in the international system of units, where "1 Pa" denotes 1 Pascal.

In illustrative embodiments, the maximum pressure generally applied by a user to a seating portion of a seat is about 90 $g/cm^2$, and the maximum pressure generally applied to a seat backrest is 70 $g/cm^2$.

In illustrative embodiments, the seat further comprises at least one measurement sheet forming the at least one measurement area and electrically connecting the at least one interdigital capacitive sensor to the at least one resistive electrode.

In illustrative embodiments, the measurement sheet thus makes it possible to connect a plurality of interdigital capacitive sensors and resistive electrodes.

In illustrative embodiments, all the interdigital capacitive sensors and resistive electrodes formed by a measurement sheet are electrically connected to one another.

In illustrative embodiments, this makes it possible to simplify the manufacture of seats comprising the measurement areas, for example, when the sheet is manufactured on a substrate.

In illustrative embodiments, at least one distance separating the at least one interdigital capacitive sensor and the at least one resistive electrode is less than 50 millimeters and greater than 10 millimeters, preferably equal to 20 millimeters.

In illustrative embodiments, an accuracy of plus or minus 2.5 millimeters is considered for determining a distance between two elements.

In illustrative embodiments, positioning an interdigital capacitive sensor and a resistive electrode in such proximity to one another increases the accuracy and reliability of the measurements obtained by their combination. The combination of these measurements is maximized when the distance between each interdigital capacitive sensor-resistive electrode pair is 20 millimeters plus or minus 2.5 millimeters.

In illustrative embodiments, the total number of interdigital capacitive sensors comprised in the seat is strictly greater than one and strictly less than six, preferably equal to four, and the total number of resistive electrodes comprised in the seat is strictly greater than one and strictly less than six, preferably equal to four.

In illustrative embodiments, the seat comprises four measurement areas, the first and second of the measurement areas being formed on the backrest and one to each side of a horizontal central plane of the backrest, the third and fourth of the measurement areas being formed on the seating portion and one to each side of a transverse central plane of the seating portion.

In illustrative embodiments:
the first measurement area comprises an interdigital capacitive sensor and a resistive electrode which are located on a same side of a vertical central plane of the backrest;
the second measurement area comprises an interdigital capacitive sensor and a resistive electrode which are located substantially along the vertical central plane;
the third measurement area comprises an interdigital capacitive sensor and a resistive electrode which are located substantially along a longitudinal central plane of the seating portion; and
the fourth measurement area comprises an interdigital capacitive sensor and a resistive electrode which are located on a same side of the longitudinal central plane.

In illustrative embodiments, this makes it possible to provide a measurement system which is a seat occupant detection system exhibiting a high reliability, called the ODS system.

In illustrative embodiments, an element, here an interdigital capacitive sensor or a resistive electrode, being located substantially along a given plane means that this element is partially located within this given plane or is distanced from it by a distance less than or equal to 5 centimeters.

In illustrative embodiments, the vertical central plane of the backrest and the longitudinal central plane of the seating portion are identical and define one and the same plane, called the plane of symmetry of the seat, which is generally the case when the backrest and the seating portion are aligned.

In illustrative embodiments, when the vertical central plane of the backrest and the longitudinal central plane of the seating portion are identical and define the plane of symmetry of the seat, the interdigital capacitive sensor comprised in the first measurement area and the interdigital capacitive sensor comprised in the fourth measurement area are located on opposite sides of the seat's plane of symmetry; furthermore, the resistive electrode comprised in the first measurement area and the resistive electrode comprised in the fourth measurement area are located on opposite sides of the seat's plane of symmetry.

In illustrative embodiments, the examples of a seat for which at least two interdigital capacitive sensors and/or at least two resistive electrodes are located in the same measurement area, or even in separate measurement areas, allow making differential measurements.

In illustrative embodiments, this makes it possible to increase robustness by filtering or eliminating specific measurements: for example, one can use a particular selection of at least two interdigital capacitive sensors and/or resistive electrodes to highlight measurements due to movements or vibrations that are slight and therefore more difficult to measure, or conversely to eliminate them and thus improve the signal-to-noise ratio.

In illustrative embodiments, the implementation of differential measurements by means of a plurality of interdigital capacitive sensors and/or resistive electrodes makes it possible to detect fidgeting movements of a user occupying the seat, or the user turning his or her head to look behind, etc.

In illustrative embodiments:
the first measurement area comprises, on each side of a vertical central plane of the backrest, an interdigital capacitive sensor and a resistive electrode;
the second measurement area comprises an interdigital capacitive sensor and a resistive electrode which are located substantially along the vertical central plane;
the third measurement area comprises an interdigital capacitive sensor and a resistive electrode which are located substantially along a longitudinal central plane of the seating portion; and
the fourth measurement area comprises, on each side of the longitudinal central plane, an interdigital capacitive sensor and a resistive electrode.

In illustrative embodiments, this makes it possible to provide a measurement system which is an occupant classification system, called the OCS system. Such an OCS system allows determining the type of user occupying the seat, for example an adult, a child, a male user, a female user, etc.

In illustrative embodiments:
the first measurement area comprises an interdigital capacitive sensor and a resistive electrode which are located substantially along a vertical central plane of the backrest;
the second measurement area comprises, on each side of the vertical central plane, an interdigital capacitive sensor and a resistive electrode;
the third measurement area comprises an interdigital capacitive sensor and a resistive electrode which are located substantially along a longitudinal central plane of the seating portion; and
the fourth measurement area comprises, on each side of the longitudinal central plane, an interdigital capacitive sensor and a resistive electrode.

In illustrative embodiments, this makes it possible to provide a measurement system which is a lumbar discomfort monitoring system, called the LF system (or "Lumbar Fit"). Such an LF system allows detecting back pain experienced by a user occupying the seat, particularly in the lumbar region, for example due to poor positioning of the user in the seat or poor adjustment of the backrest and/or seating portion of the seat.

In illustrative embodiments, it is thus possible to provide the user with a signal or information enabling the user to react, for example to avoid pinched vertebrae and, in the longer term, back pain.

In illustrative embodiments:
the first measurement area comprises an interdigital capacitive sensor and a resistive electrode which are located substantially along a vertical central plane of the backrest;

the second measurement area comprises an interdigital capacitive sensor and a resistive electrode which are located substantially along the vertical central plane;

the third measurement area comprises, on each side of a longitudinal central plane of the seating portion, an interdigital capacitive sensor and a resistive electrode; and the fourth measurement area comprises, on each side of the longitudinal central plane, an interdigital capacitive sensor and a resistive electrode.

In illustrative embodiments, this makes it possible to provide a measurement system which is a pelvic discomfort monitoring system, known as the PD system (for "Pelvis Drift"). Such a PD system makes it possible to detect any pelvic pain experienced by a user occupying the seat, in particular in the region of the pelvis, the pelvic area, including the lower abdomen and the genital area, for example due to poor positioning of the user in the seat or poor adjustment of the backrest and/or seating portion of the seat.

In illustrative embodiments, it is thus possible to provide the user with a signal or information enabling the user to react, for example to avoid pinching in the legs or hips.

In illustrative embodiments:
the first measurement area comprises, on each side of a vertical central plane of the backrest, an interdigital capacitive sensor and a resistive electrode;

the second measurement area comprises, on each side of the vertical central plane, an interdigital capacitive sensor and a resistive electrode, the second measurement area further comprising an interdigital capacitive sensor and a resistive electrode along the vertical central plane;

the third measurement area comprises, on each side of a longitudinal central plane of the seating portion, an interdigital capacitive sensor and a resistive electrode, the third measurement area further comprising an interdigital capacitive sensor and a resistive electrode along the longitudinal central plane; and the fourth measurement area comprises, on each side of the longitudinal central plane, an interdigital capacitive sensor and a resistive electrode.

In illustrative embodiments, this makes it possible to provide a measurement system that combines several types of measurement systems, namely an OCS classification system, an LF lumbar discomfort monitoring system, and a PD pelvic discomfort monitoring system. This thus allows determining a classification of a user occupying the seat while monitoring for possible lumbar pain and pelvic pain in the user.

In illustrative embodiments, the positioning of the interdigital capacitive sensors and resistive electrodes in the measurement systems mentioned above makes it possible to provide an anthropometric device, meaning capable of detecting and identifying the majority of the physiologies and positions permitted by a seat user.

In illustrative embodiments, at least one interdigital capacitive sensor is suitable for measuring a capacitance greater than 300 picofarads and less than 3500 picofarads, preferably less than 2500 picofarads if the at least one interdigital capacitive sensor is located in the second measurement area or in the fourth measurement area; and at least one resistive electrode is suitable for measuring a pressure of less than 300 g/cm$^2$, preferably less than 30 g/cm$^2$ if the resistive electrode is located in the first measurement area, preferably greater than 30 g/cm$^2$ and less than 100 g/cm$^2$ if the resistive electrode is located in the second measurement area, preferably greater than 65 g/cm$^2$ if the resistive electrode is located in the third measurement area, preferably greater than 10 g/cm$^2$ and less than 50 g/cm$^2$ if the resistive electrode is located in the fourth measurement area.

In illustrative embodiments, "pF" indicates the unit of measurement for capacitance, expressed in picofarads.

In illustrative embodiments, this makes it possible to provide capacitance measurements and pressure measurements with a sensitivity that takes into account human physiology, and in particular, an optimal sensitivity for implementing the detection of a human user in the seat, the determination of a type of seat occupant, and the monitoring for lumbar pain and/or pelvic pain of a human user in the seat.

In illustrative embodiments, a controller arranged so as to be connected to the at least one measurement area of a seat according to any one of the preceding specific examples, the controller being configured for determining a type of user occupying the seat, detecting the user, monitoring for lumbar pain of the user and/or monitoring for pelvic pain of the user.

In illustrative embodiments, the controller comprises computer means, for example hardware comprising a processor, a microprocessor, or a board of sensors, the hardware being arranged to implement a computer program such as software or an algorithm.

In illustrative embodiments, the software or algorithm uses an intelligent method of data fusion, based on measurements made by at least one interdigital capacitive sensor and at least one resistive electrode, preferably located near one another.

In illustrative embodiments, such processing of these data makes it possible, from these measurements, to evaluate and provide an accurate detection of a user occupying the seat and to classify the type of user.

In illustrative embodiments, this software or algorithm comprises instructions for implementing a detection of an occupant in the seat when the measurement system comprising the at least one measurement area is an ODS system, when the instructions are executed by the controller hardware.

In illustrative embodiments, this software or algorithm comprises instructions for implementing a classification of an occupant in the seat when the measurement system comprising the at least one measurement area is an OCS system, when the instructions are executed by the controller hardware.

In illustrative embodiments, this software or algorithm comprises instructions for implementing a lumbar discomfort monitoring of an occupant in the seat when the measurement system comprising the at least one measurement area is an LF system, and when the instructions are executed by the controller hardware.

In illustrative embodiments, this software or algorithm comprises instructions for implementing a pelvic discomfort monitoring of an occupant in the seat when the measurement system comprising the at least one measurement area is a PD system, and when the instructions are executed by the controller hardware.

In illustrative embodiments, the controller is an engine control unit which is external to the seat.

In illustrative embodiments, an engine control unit, or ECU, is a control unit configured to receive data coming from sensors of any type arranged in the vehicle, and in the present case, interdigital capacitive sensors and resistive electrodes comprised in the at least one measurement area to which the controller is arranged to be connected.

In illustrative embodiments, in addition, an ECU may adapt or modify parameters of the engine or of the vehicle in general, for example engine torque, cruise control, automatic gear shifting, emission control, fuel distribution, or the ignition timing of the vehicle's engine. An ECU may also adapt or modify parameters of the parameters of other devices installed in the vehicle, for example a loudspeaker, an airbag, a camera, an air conditioning system, etc.

In illustrative embodiments, a measurement system comprising a seat according to any one of the preceding specific examples and a controller according to any one of the preceding specific examples.

In illustrative embodiments, the seats, the controllers, and the measurement systems to which the present application relates have high ergonomics and can be produced at a reduced cost for large-scale distribution.

In illustrative embodiments, a measurement method implemented by means of a seat comprising a backrest, a seating portion connected to the backrest, at least one measurement area defined on the backrest and/or on the seating portion, the at least one measurement area comprising at least one interdigital capacitive sensor capable of measuring a distance or movement of a user occupying the seat, the at least one measurement area of the seat being connected to a controller configured for determining a type of user occupying the seat or for detecting the user, the method comprising:
- calibrating the at least one interdigital capacitive sensor by performing a measurement when the seat is not occupied;
- determining, with the at least one calibrated interdigital capacitive sensor, a plurality of distances or movements of the user when the user is occupying the seat; and
- detecting the user or determining the type of user, based on a comparison between several of the determined distances or movements.

In illustrative embodiments, the plurality of distances or movements may be determined by a same sensor or by several same sensors at different given times. The plurality of distances or movements may also be determined by several sensors at the same time. The plurality of distances or movements may also be determined by several sensors at several times.

In illustrative embodiments, this provides a quantitative means of detecting a user in a seat or of determining a type of user occupying the seat.

In illustrative embodiments, the at least one measurement area further comprises at least one resistive electrode capable of measuring a contact pressure of a user occupying the seat, the method further comprising:
- determining, with the at least one calibrated resistive electrode, a plurality of contact pressures of the user; and
- fusing several of the determined contact pressures with several of the determined distances or movements in order to form a set of fused measurements,
- the user detection or the user type determination being implemented based on a comparison between several of the fused measurements.

In illustrative embodiments, this improves the accuracy and reliability of the detection of a user in the seat or the determination of the user type, by combining several types of measurements.

In illustrative embodiments, the controller is further configured to monitor for lumbar pain of the user and/or pelvic pain of the user, the method further comprising:

monitoring for lumbar pain and/or pelvic pain of the user based on an average and/or a gradient of several of the determined distances or movements.

In illustrative embodiments, a gradient is equivalent to a slope or a derivative of the evolution over time of the determined distances or movements.

In illustrative embodiments, the monitoring for lumbar pain and/or pelvic pain of the user may also be done on the basis of an average and/or gradient of determined pressures.

In illustrative embodiments, this makes it possible to improve the reliability of a monitoring for pelvic and/or lumbar discomfort in a user occupying the seat, based on variations in the measurements made.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Unless otherwise indicated, elements that are similar or identical in multiple figures bear the same reference symbols and have identical or similar characteristics; therefore for simplicity these identical elements are generally not described again.

For the most part, the drawings and description below contain elements that are certain in nature. They therefore not only serve to provide a better understanding of this disclosure, they also contribute to its definition where appropriate.

Figure 1:
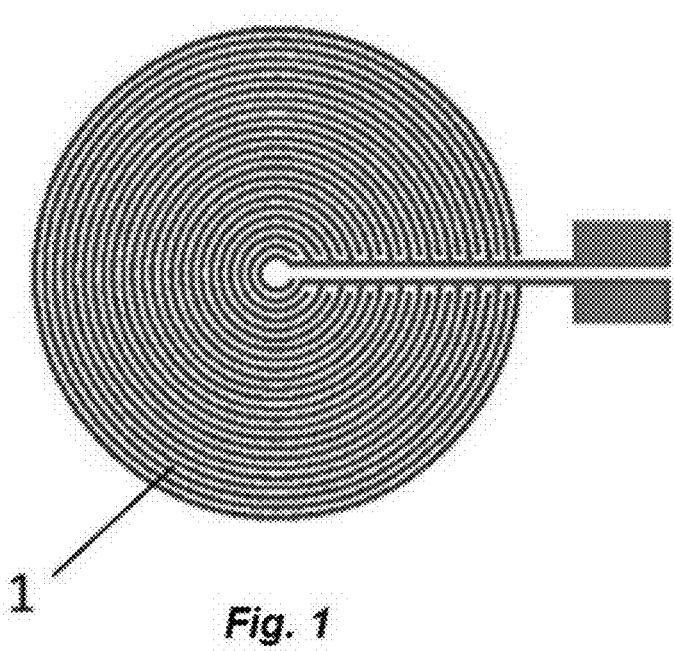
FIG. 1 shows an example of an interdigital capacitive sensor of the circular type.

Reference is now made to FIG. 1 which represents an example of an interdigital capacitive sensor of the circular type.

The capacitive sensor 1 shown is a circular capacitive sensor which is for example formed of a printed circuit board, and/or comprises a ceramic substrate as well as various conductive sheets in titanium, copper, nickel, or gold.

An interdigital capacitive sensor may also have different types of geometry, for example spiral, concentric, or elliptical. Preferably, the capacitive sensor 1 and the sensor examples having the aforementioned geometries have rotational symmetry such that the capacitance of the sensor is less sensitive to the relative orientation than sensors of non-symmetrical geometry, for example a sensor of rectangular geometry.

Figure 2:
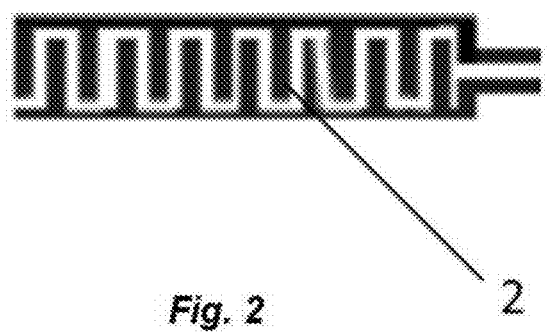
FIG. 2 shows an example of an interdigital capacitive sensor of the rectangular type.

Reference is now made to FIG. 2, which represents an example of a rectangular interdigital capacitive sensor.

The capacitive sensor 2 shown is a rectangular capacitive sensor which is for example formed of the same elements as the circular interdigital capacitive sensor described above.

Advantageously, a rectangular interdigital capacitive sensor has a small volume and makes it possible to measure rapid variations, on the order of a microsecond.

In addition, a rectangular interdigital capacitive sensor makes it possible to measure a relative compression comprised between 0 and 0.25, providing sufficient sensitivity to measure micro-vibrations, and for example micro-vibrations resulting from slight movements or fidgeting of a seat user.

Figure 3:
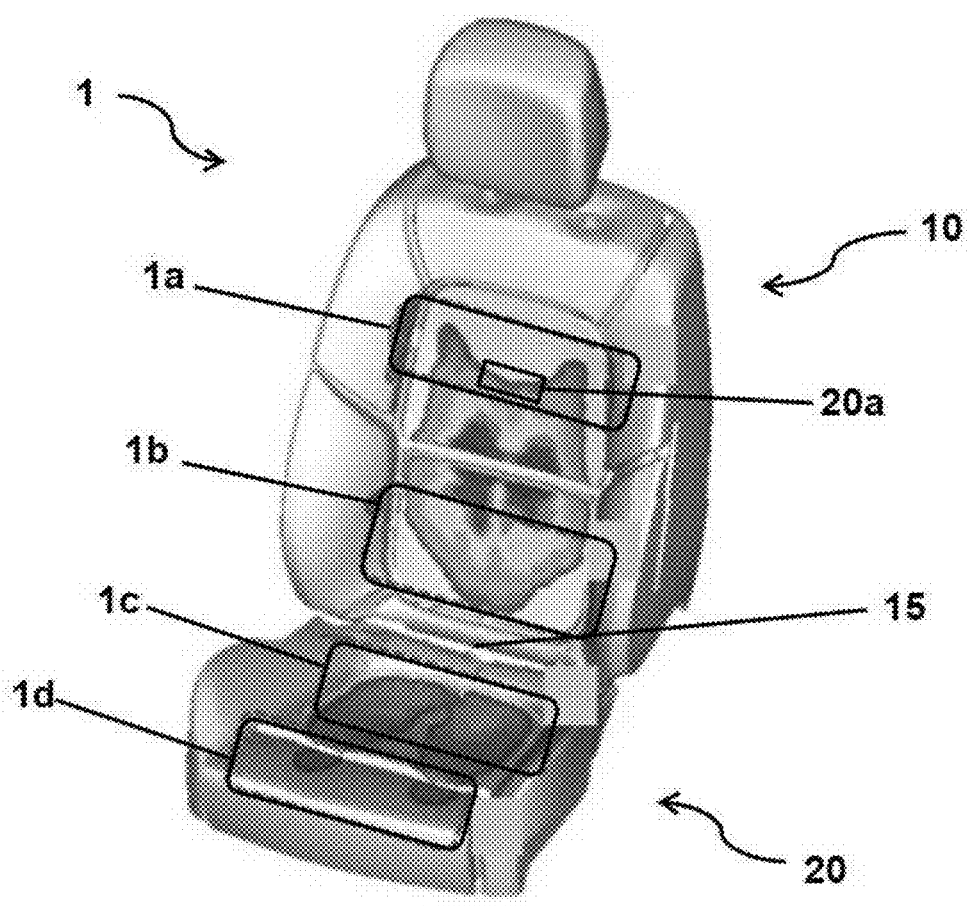
FIG. 3 shows an example of measurement areas of a seat.

Reference is now made to FIG. 3, which shows an example of several measurement areas formed in a backrest 10 and in a seating portion 20 of a seat 1.

The seat 1 comprises a seating portion 20 on which a user sits and a backrest 10 against which the user can lean part of his or her back. The backrest 10 is connected to the seating portion 20 by a connecting element 15, for example a hinged connection along a transverse axis, which separates the backrest 10 from the seating portion 20. This hinged connection can allow the backrest 10 to be moved relative to the seating portion 20 by means of a rotational movement.

The seat 1 may also comprise a headrest against which the user can lean part of his or her neck.

When a user is occupying the seat 1, part of the user's body is generally in contact with at least the seating portion 20 or the backrest 10 of the seat 1.

Measurement areas may be formed partially or completely on or in the seat 1, on or in the seating portion 10 of the seat 1 and/or on or in the backrest 20 of the seat 1. For example, the measurement areas are formed by a foam comprised in the seat 1.

In another example, measurement areas are formed partially or completely by one or more sheets placed in the seat 1. In particular, one or more sheets are placed in the seating portion 10 of the seat 1 and in the backrest 20 of the seat 1.

In the example presented here, four measurement areas are formed in the seat 1, two of these measurement areas formed on the backrest 10 and two other measurement areas formed on the seating portion 20.

In this example, a first measurement area 1a is formed in an upper part of the backrest 10 and a second measurement area 1b is formed in a lower part of the backrest 10. A third measurement area 1c is formed in a first part of the seating portion 20, this first part of the backrest being located near the connecting element 15. A fourth measurement area 1d is formed in a second part of the seating portion 20, this fourth measurement area 1d being more distanced from the connecting element 15 than the third measurement area 1c.

During normal use, when a user is sitting on the seat 1, the user's back is resting against the backrest 10 and the buttocks and part of the user's legs are resting on the seating portion 20.

In particular, the position of the user is such that the user's shoulders are in contact with the first measurement area 1a, the lumbar region of the user is in contact with the second measurement area 1b, the user's buttocks are in contact with the third measurement area 1c, and the user's hamstrings are in contact with the fourth measurement area 1d.

For example, the third measurement area 1c may comprise a surface of a sheet which includes one or more interdigital capacitive sensors and/or one or more resistive electrodes, arranged on the seating portion 20.

This makes it possible to determine, in an occasional or continuous manner, a pressure distribution zone on the surface of the third measurement area 1c. In particular, this distribution zone is determined when a user is seated on the surface of the sheet comprised in the seating portion 20.

Advantageously, the measurement areas 1a, 1b, 1c, and 1d are arranged so that they are located near the regions of the seat 1 where greater and more frequent variations in pressure exerted by a user are expected due to the presence of the user.

According to another example, two measurement areas are formed in the seat 1, one a measurement area formed on the backrest 10 and the other a measurement area formed on the seating portion 20.

According to yet another example, a single measurement area is formed in the seat 1, the measurement area being formed either on both the backrest 10 and the seating portion 20, or on only the backrest 10 or the seating portion 20.

Figure 4:
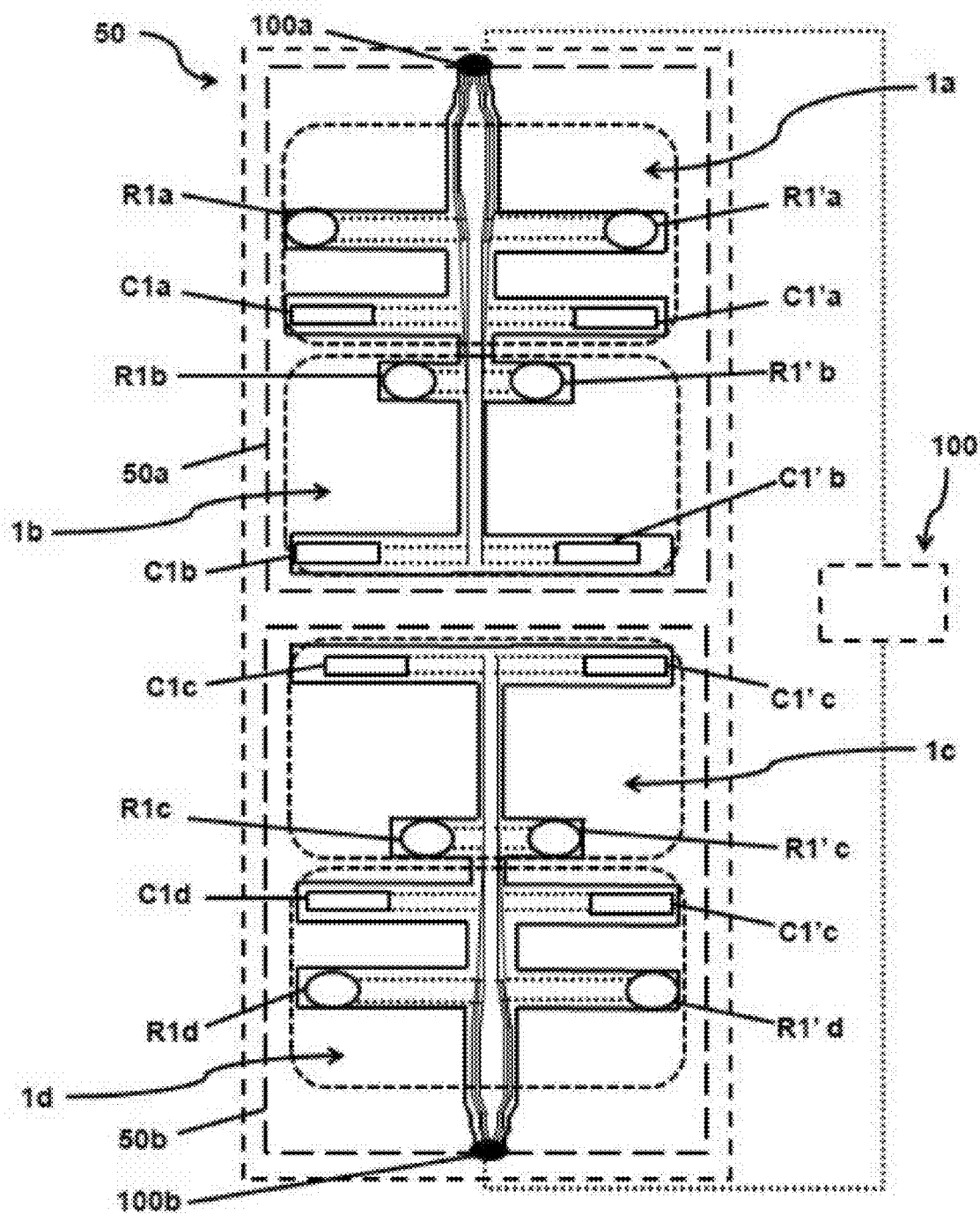
FIG. 4 shows an example of a sheet comprising sensors for measurement areas of a seat.

Reference is now made to FIG. 4, which illustrates an example of a sheet comprising sensors for measurement areas of a seat or elements of a seat according to one exemplary embodiment.

As illustrated, a sheet 50 may comprise a first part 50a and a second part 50b which are connected together. In one example, these two parts have an identical structure, and are arranged symmetrically with respect to each other.

In one example, the sheet 50 is placed on the seat so that it covers the four measurement areas 1a, 1b, 1c and 1d described above. In the present case, the sheet 50 is arranged so that the first part 50a covers the backrest of the seat at measurement areas 1a and 1b, while the second part 50b covers the seating portion of the seat at measurement areas 1c and 1d.

According to one example, the sheet 50 comprises at least one interdigital capacitive sensor in each measurement area of the seat. Preferably, the sheet 50 comprises two interdigital capacitive sensors in each measurement area of the seat. The interdigital capacitive sensor(s) are configured to determine a distance from the user's body or a movement of the body, relative to the sensor(s) and more generally relative to the seat.

In addition, the sheet 50 comprises at least one resistive electrode in each measurement area of the seat. The resistive electrode(s) are configured to determine a contact pressure of the user's body or a movement of the body, relative to the electrode(s) and more generally relative to the seat.

In one example, the sheet 50 comprises two resistive electrodes in each measurement area of the seat. In a non-limiting manner, other variants in the placement of the interdigital capacitive sensors and resistive electrodes may define the sheet 50. Different variants are detailed in the remainder of the description, each of these variants enabling the measurement of different physiologies of a vehicle seat user.

Furthermore, in one variant, the seat comprises two measurement sheets, the first of these sheets forming two measurement areas on the backrest of the seat and the second of these sheets forming two measurement areas on the seating portion of the seat, the first and second sheets able to be linked or connected together.

In another variant, the seat comprises four measurement sheets, possibly completely or partially linked or connected to each other, each sheet forming a measurement area, two of the sheets covering the backrest of the seat and the two other sheets covering the seating portion of the seat.

As illustrated in FIG. 4, the first part 50a of the sheet 50 covers measurement areas 1a and 1b and the second part 50b of the sheet 50 covers measurement areas 1c and 1d.

In one example, at least one interdigital capacitive sensor and/or at least one resistive electrode forms part of the sheet, for example on or in a substrate from which the sheet is formed. This makes it possible to provide a single technology, which is easier to manufacture.

In particular, each of the parts 50a and 50b of the measurement sheet 50 comprises one or more metal tracks forming the electrical connection between the interdigital capacitive sensor(s) and the resistive electrode(s) that it comprises.

In one example, the measurement sheet 50 or one of its parts may be formed by means of a molding suitable for facilitating detection of the physiology of a human user.

Measurement area 1a comprises two resistive electrodes Ria and R1'a and two interdigital capacitive sensors C1a and C1'a. Measurement area 1b comprises two resistive electrodes R1b and R1'b and two interdigital capacitive sensors C1b and C1'b.

In one example, resistive electrodes Ria and R1'a and resistive electrodes R1b and R1'b are symmetrically arranged in pairs relative to a vertical plane through the seat or the seat backrest.

In particular, this vertical plane is a central vertical plane of the seat or of the seat backrest, meaning that it passes approximately through their middle, and can define a plane of symmetry for them.

In addition, interdigital capacitive sensors C1a and C1'a and interdigital capacitive sensors C1b and C1'b are symmetrically arranged in pairs relative to this central vertical plane.

Measurement area 1c comprises two interdigital capacitive sensors C1c and C1'c and two resistive electrodes R1c and R1'c. Measurement area 1d comprises two interdigital capacitive sensors C1d and C1'd and two resistive electrodes R1d and R1'd.

In one example, resistive electrodes R1c and R1'c and resistive electrodes R1d and R1'd are symmetrically arranged in pairs relative to a vertical plane through the seat or the seating portion of the seat.

In particular, this vertical plane is a central vertical plane of the seat or of the seating portion of the seat, meaning that it passes approximately through their middle, and can define a plane of symmetry for them.

Similarly, interdigital capacitive sensors C1c and C1'c and interdigital capacitive sensors C1d and C1'd are symmetrically arranged in pairs relative to the central vertical plane of the seat or of the seating portion of the seat.

According to one example, the sheet 50 is electrically connected to a controller 100.

According to various examples, the controller 100 is a processor, a microprocessor, a processing circuit, for example a system on chip, or even a computer.

The controller 100 comprises hardware in order to be able to process data, in particular measurements from the interdigital capacitive sensors and resistive electrodes described above, and configured by means of one or more algorithms or software which allow determining a physiology of a user occupying the seat, based on these measurements.

In the example illustrated, an electrical connection is established between the sheet 50 and the controller 100 by means of two separate connections: a first electrical connection 100a made between the first part 50a of the sheet and the controller 100, and a second electrical connection 100b made between the second part 50b of the sheet and the controller 100.

The measurement sheet 50 may include one or more variants of terminals for implementing the electrical connection 100a and/or 100b between the parts of the sheet and the controller 100. These variants may be combined with each other at several positions of a conductive track formed by the measurement sheet 50.

A first variant, preferred when the sheet is produced on a PCB ("Printed Circuit Board"), is a terminal comprising a single ZIF-type ("Zero Insertion Force") connector, with for example a pitch of 1 millimeter. Advantageously, the PCB is a "Flex PCB", which is produced on a flexible substrate, and comprises hybrid electronics.

A second variant, advantageous when the measurement sheet 50 is suitable for being connected in its entirety to the controller 100, is a terminal comprising a single crimp connector, for example with a pitch of 1.27 millimeters.

A third variant, advantageous when the measurement sheet 50 is locally separated into two parts, is a terminal comprising two crimp connectors, for example with a pitch of 1.27 millimeters, which provides improved efficiency.

When combined, the measurement sheet 100 may respectively comprise, and in this order, a terminal comprising the first variant at one end, then the second variant and the third variant.

According to an example not shown, an electrical connection may be implemented between the first part 50a and the second part 50b of the sheet.

According to an example not shown, the first part 50a and the second part 50b may define distinct parts of the sheet which are not interconnected. In this case, the first part 50a and the second part 50b may each be electrically connected to the controller 100 by means of one or more electrical connections.

Figure 5A:
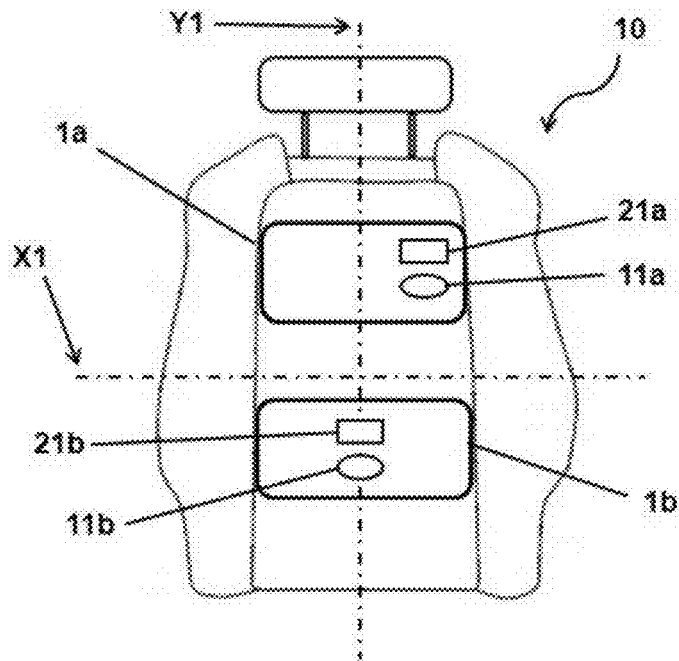
FIG. 5a shows an example of sensor positioning in a backrest of a seat according to a first variant embodiment.
Figure 5B:
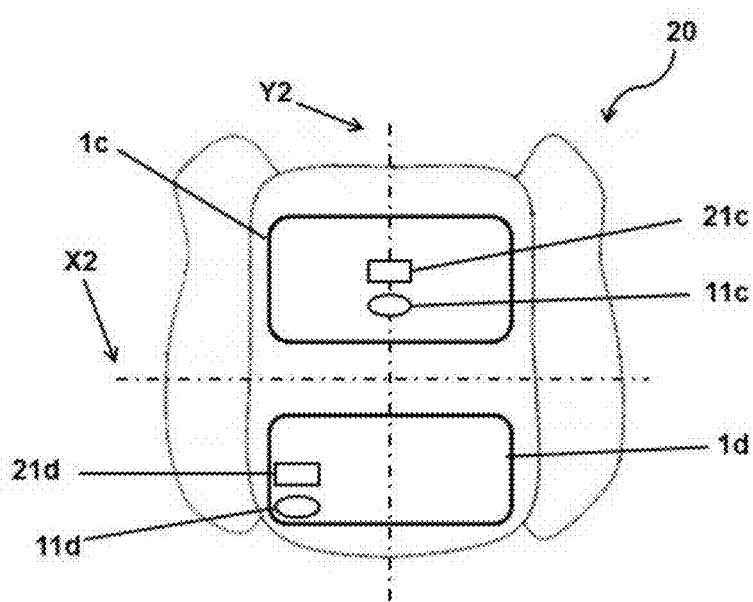
FIG. 5b shows an example of sensor positioning in a seating portion of a seat according to the first variant.

Reference is now made to FIGS. 5a and 5b, which show a first alternative embodiment of sensor positioning, in a backrest of a seat in FIG. 5a and in a seating portion of the seat in FIG. 5b.

According to this first variant, the seat comprises a first measurement system providing an occupant detection system, called an ODS system. The ODS system comprises, in total, four interdigital capacitive sensors 21a, 21b, 21c, and 21d as well as four resistive electrodes 11a, 11b, 11c, and 11d, so as to provide a measurement system comprising four measurement areas having an interdigital capacitive sensor and a resistive electrode positioned in each one.

In FIG. 5a, sensor 21a and electrode 11a are positioned close to each other in the first measurement area 1a, the first measurement area 1a being located above a horizontal central plane X1 of the backrest 10. More precisely, sensor 21a and electrode 11a are positioned in the first measurement area 1a so as to be located on a same side of a vertical central plane Y1 of the backrest 10, the vertical central plane Y1 being substantially perpendicular to the horizontal central plane X1 and preferably coincident with a plane of symmetry of the backrest 10.

Herein, for all the alternative embodiments of sensor positioning, a "close" positioning of an interdigital capacitive sensor and a resistive electrode means that the distance between them is less than 50 millimeters and greater than 10 millimeters. Advantageously, the accuracy and reliability of the measurements obtained by a combination of an interdigital capacitive sensor and a resistive electrode positioned close to each other are optimal when the distance between them is about 20 millimeters.

In addition, in FIG. 5a, sensor 21b and electrode 11b are positioned close to each other in the second measurement area 1b, the second measurement area 1b being located below the horizontal central plane X1. More precisely, sensor 21b and electrode 11b are positioned in the second measurement area 1b so as to be positioned along a straight line parallel to or within a plane parallel to the vertical central plane Y1, or within this vertical central plane Y1, in other words approximately in the middle of the second measurement area 1b.

In FIG. 5b, sensor 21c and electrode 11c are positioned close to each other in the third measurement area 1c, the third measurement area 1c being located at the rear of the seating portion 20, meaning behind a transverse central plane X2 of the seating portion. More precisely, sensor 21c and electrode 11c are positioned in the third measurement area 1c so as to be positioned along a straight line parallel to or within a plane parallel to a longitudinal central plane Y2 of the seating portion 20, or within the longitudinal central plane Y2, this longitudinal central plane Y2 being substantially perpendicular to the transverse central plane X2, passing approximately through the middle of the third measurement area 1c.

Furthermore, in FIG. 5b, sensor 21d and electrode 11d are positioned close to each other in the fourth measurement area 1d, the fourth measurement area 1d being located at the front of the seating portion 20, meaning in front of the transverse central plane X2. More precisely, sensor 21d and electrode 11d are positioned in the fourth measurement area 1d such that they are located on a same side of the longitudinal central plane Y2 of the seating portion 20.

In one example, the vertical central plane Y1 and the longitudinal central plane Y2 are parallel and respectively define a plane of symmetry of the backrest 10 and a plane of symmetry of the seating portion 20. Preferably, these two planes of symmetry define a common plane of symmetry of the seat comprising the backrest 10 and the seating portion 20. Preferably, sensors 21a and 11a are located on one side of this common plane of symmetry, while sensors 21d and 11d are located on the other side of this common plane of symmetry.

In one example, the number and positioning of the interdigital capacitive sensors and of the resistive electrodes for this first measurement system, called the ODS system, provide improved reliability when a detection of an occupant is implemented.

In one example, the ergonomics of such an ODS system are improved because only one interdigital capacitive sensor and only one resistive electrode are necessary in the fourth measurement area in order to detect the presence of a user based on only one of his or her legs or only one foot.

Figure 6A:
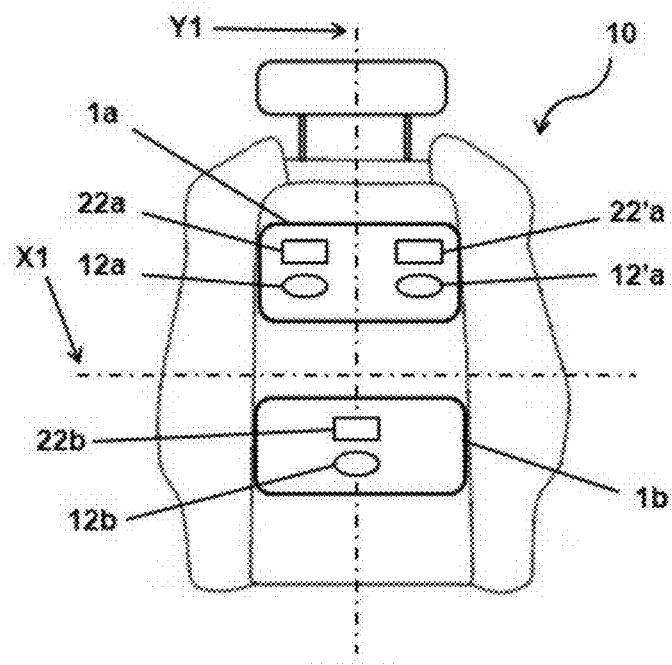
FIG. 6a shows an example of sensor positioning in a backrest of a seat according to a second variant embodiment.
Figure 6B:
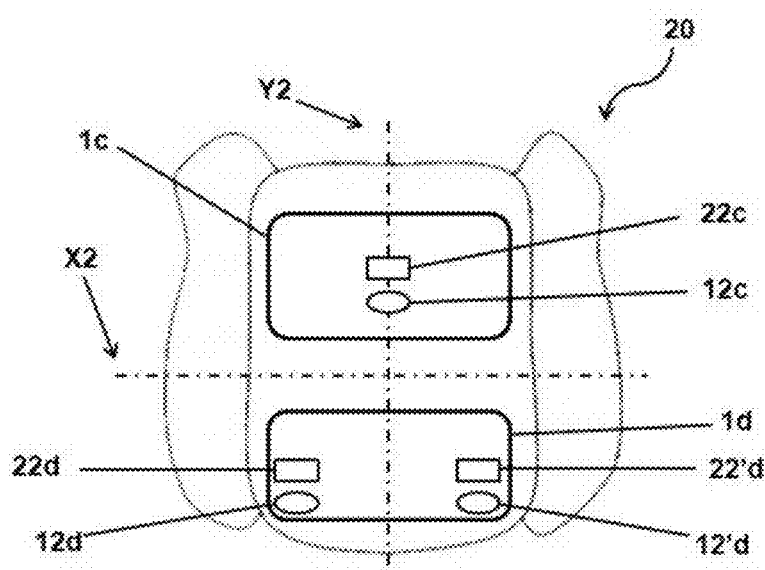
FIG. 6b shows an example of sensor positioning in a seating portion of a seat according to the second variant.

Reference is now made to FIGS. 6a and 6b, which show a second alternative embodiment of sensor positioning, in the backrest in FIG. 6a and in the seating portion in FIG. 6b.

According to this second variant, the seat comprises a second measurement system providing an occupant classification system, called the OCS system.

The OCS system comprises, in total, six interdigital capacitive sensors 22a, 22'a, 22b, 22c, 22d, and 22'd, as well as six resistive electrodes 12a, 12'a, 12c, 12d, and 12'd, providing a measurement system comprising four measurement areas with either two interdigital capacitive sensors and two resistive electrodes, or one interdigital capacitive sensor and one resistive electrode, positioned in each area.

In FIG. 6a, sensors 22a and 22'a are positioned in the first measurement area 1a, one to each side of the vertical central plane Y1. Resistive electrode 12a is positioned near sensor 22a and resistive electrode 12'a is positioned near sensor 22'a. Resistive electrodes 12a and 12'a are positioned in the first measurement area 1a as well, one to each side of the vertical central plane Y1.

In addition, in FIG. 6a, sensor 22b and electrode 12b are positioned close to each other in the second measurement area 1b, the second measurement area 1b being located below the horizontal central plane X1. More precisely, sensor 21b and electrode 11b are positioned in the second measurement area 1b so as to be located along a straight line parallel to or within a plane parallel to the vertical central plane Y1, or within this vertical central plane Y1, in other words approximately in the middle of the second measurement area 1b.

In FIG. 6b, sensor 22c and electrode 12c are positioned close to each other in the third measurement area 1c, the third measurement area 1c being located at the rear of the seating portion 20, in other words behind the transverse central plane X2. More precisely, sensor 22c and electrode 12c are positioned in the third measurement area 1c so as to be located along a straight line parallel to or within a plane parallel to the longitudinal central plane Y2, in other words approximately in the middle of the third measurement area 1d.

In addition, in FIG. 6b, sensors 22d and 22'd are positioned in the fourth measurement area 1d, one to each side of the longitudinal central plane Y2. Resistive electrode 12d is positioned near sensor 22d and resistive electrode 12'd is positioned near sensor 22'd. Resistive electrodes 12d and 12'd are positioned in the fourth measurement area 1d as well, one to each side of the longitudinal central plane Y2.

In one example, the number and positioning of the interdigital capacitive sensors and of the resistive electrodes for this second measurement system, called the OCS system, provide improved reliability and increased precision when implementing a classification of an occupant. This also allows providing an OCS system in which an incorrect classification of a child as an adult or an incorrect classification of an adult as a child is avoided.

Figure 7A:
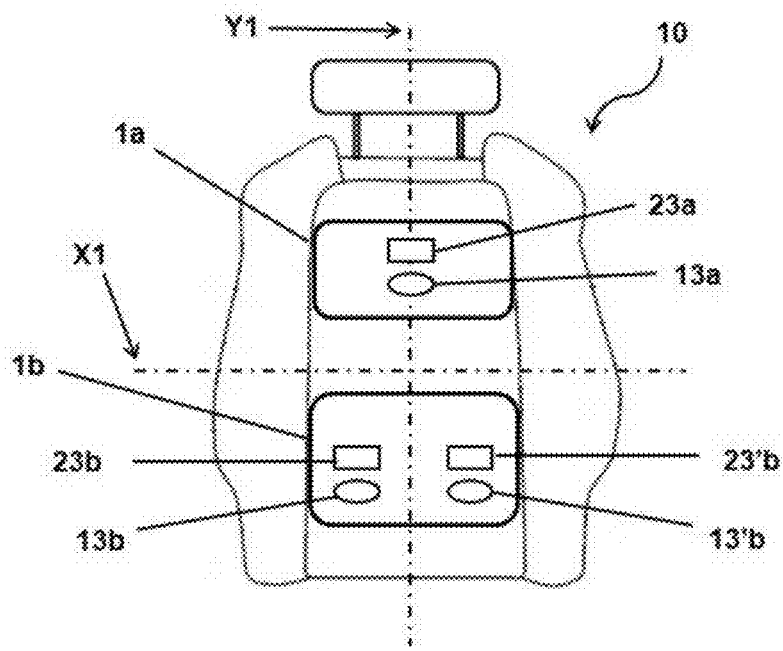
FIG. 7a shows an example of sensor positioning in a backrest of a seat according to a third variant embodiment.
Figure 7B:
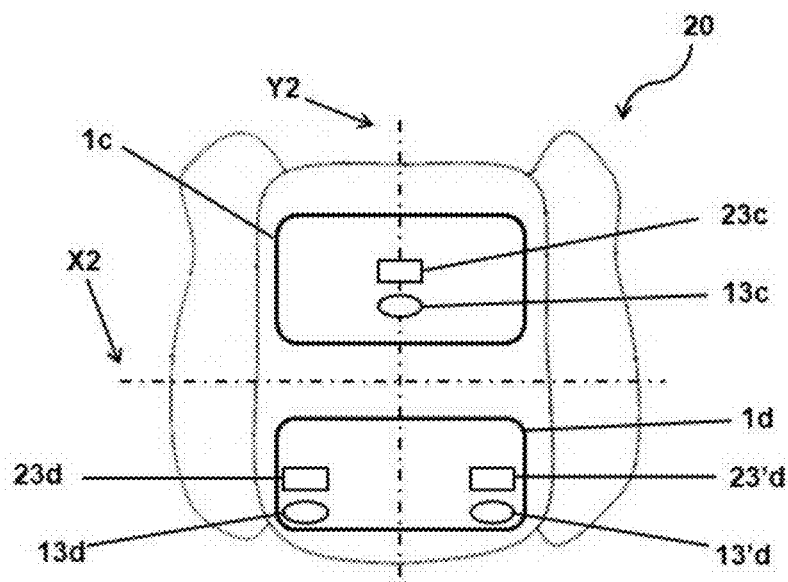
FIG. 7b shows an example of sensor positioning in a seating portion of a seat according to the third variant.

Reference is now made to FIGS. 7a and 7b, which represent a third alternative embodiment of sensor positioning, in the backrest in FIG. 7a and in the seating portion in FIG. 7b.

According to this third variant, the seat comprises a third measurement system providing a lumbar discomfort monitoring system, called the LF system.

The LF system comprises, in total, six interdigital capacitive sensors 23a, 23b, 23'b, 23c, 23d, and 23'd, as well as six resistive electrodes 13*a*, 13*b*, 13'*b*, 13*c*, 13*d*, and 13'*d*, providing a measurement system comprising four measurement areas with either one interdigital capacitive sensor and one resistive electrode, or two interdigital capacitive sensors and two resistive electrodes, positioned in each area.

In FIG. 7*a*, sensor 23*a* and electrode 13*a* are positioned close to each other in the first measurement area 1*a* and so as to be located along a line parallel to or within a plane parallel to the vertical central plane Y1, or within this vertical central plane Y1, in other words approximately in the middle of the first measurement area 1*a*.

In addition, in FIG. 7*a*, sensors 23*b* and 23'*b* are positioned in the second measurement area 1*b* one to each side of the vertical central plane Y1. Resistive electrode 13*b* is positioned near sensor 23*b* and resistive electrode 13'*b* is positioned near sensor 23'*b*. Resistive electrodes 13*b* and 13'*b* are positioned in the second measurement area 1*b* as well, one to each side of the vertical central plane Y1.

In FIG. 7*b*, sensor 23*c* and electrode 13*c* are positioned close to each other in the third measurement area 1*c*, behind the transverse central plane X2. More precisely, sensor 23*c* and electrode 13*c* are positioned in the third measurement area 1*c* so as to be positioned along a line parallel to or within a plane parallel to the longitudinal central plane Y2, in other words approximately in the middle of the third measurement area 1*c*.

In addition, in FIG. 7*b*, sensors 23*d* and 23'*d* are positioned in the fourth measurement area 1*d*, one to each side of the longitudinal central plane Y2. Resistive electrode 13*d* is positioned near sensor 23*d* and resistive electrode 13'*d* is positioned near sensor 23'*d*. Resistive electrodes 13*d* and 13'*d* are positioned in the fourth measurement area 1*d* as well, one to each side of the longitudinal central plane Y2.

In one example, the number and positioning of the interdigital capacitive sensors and of the resistive electrodes for this third measurement system, called the LF system, provide a dynamic and personalized system for monitoring for lumbar pain that a user of the seat may experience.

Figure 8A:
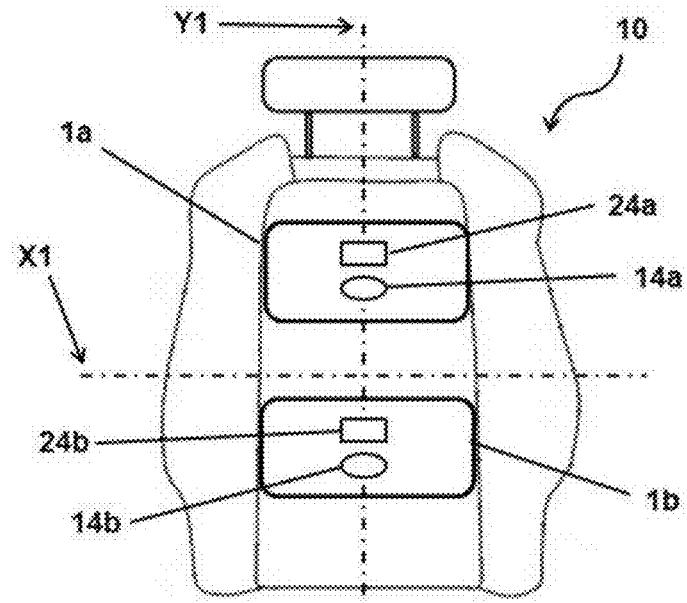
FIG. 8a shows an example of sensor positioning in a backrest of a seat according to a fourth variant embodiment.
Figure 8B:
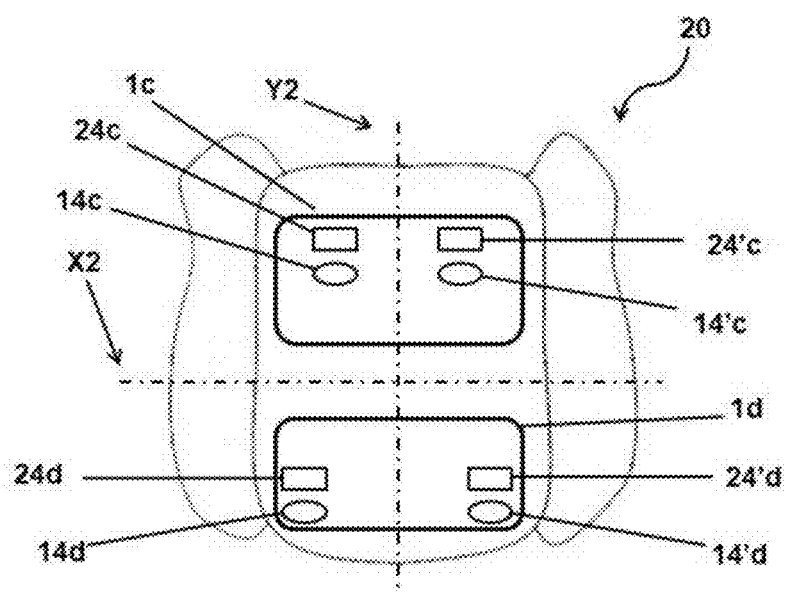
FIG. 8b shows an example of sensor positioning in a seating portion of a seat according to the fourth embodiment.

Reference is now made to FIGS. 8*a* and 8*b*, which show a fourth alternative embodiment of sensor positioning, in the backrest in FIG. 8*a* and in the seating portion in FIG. 8*b*.

According to this fourth variant, the seat comprises a third measurement system providing a pelvic discomfort monitoring system, called the PD system.

The PD system comprises, in total, six interdigital capacitive sensors 24*a*, 24*b*, 24*c*, 24'*c*, 24*d*, and 24'*d* as well as six resistive electrodes 14*a*, 14*b*, 14*c*, 14'*c*, 14*d*, and 14'*d*, providing a measurement system comprising four measurement areas with either one interdigital capacitive sensor and one resistive electrode, or two interdigital capacitive sensors and two resistive electrodes, positioned in each area.

In FIG. 8*a*, sensor 24*a* and electrode 14*a* are positioned close to each other in the first measurement area 1*a* and so as to be located along a line parallel to or within a plane parallel to the vertical central plane Y1, or within this vertical central plane Y1, in other words approximately in the middle of the first measurement area 1*a*.

In addition, in FIG. 8*a*, sensor 24*b* and electrode 14*b* are positioned close to each other in the second measurement area 1*b* and so as to be located along a line parallel to or within a plane parallel to the vertical central plane Y1, or within this vertical central plane Y1, in other words approximately in the middle of the second measurement area 1*b*.

In FIG. 8*b*, sensors 24*c* and 24'*c* are positioned in the third measurement area 1*c*, one to each side of the longitudinal central plane Y2. Resistive electrode 14*c* is positioned near sensor 24*c* and resistive electrode 14'*c* is positioned near sensor 23'*c*. Resistive electrodes 14*c* and 14'*c* are positioned in the third measurement area 1*c* as well, one to each side of the longitudinal central plane Y2.

In addition, in FIG. 8*b*, sensors 24*d* and 24'*d* are positioned in the fourth measurement area 1*d*, one to each side of the longitudinal central plane Y2. Resistive electrode 14*d* is positioned near sensor 24*d* and resistive electrode 14'*d* is positioned near sensor 24'*d*. Resistive electrodes 14*d* and 14'*d* are positioned in the fourth measurement area 1*d* as well, one to each side of the longitudinal central plane Y2.

In one example, the number and positioning of the interdigital capacitive sensors and of the resistive electrodes for this fourth measurement system, called the PD system, provide a dynamic and personalized system for monitoring for pelvic pain that a user of the seat may experience.

Figure 9A:
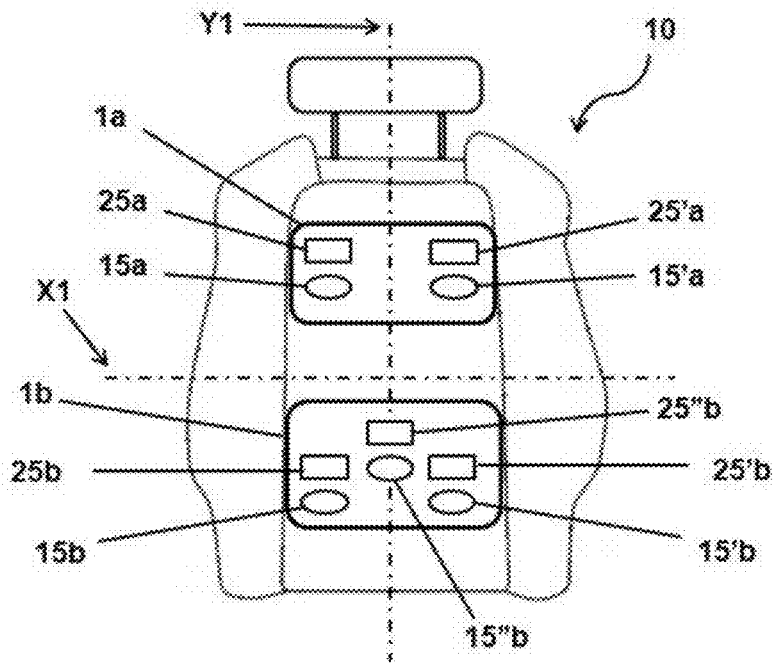
FIG. 9a shows an example of sensor positioning in a backrest of a seat according to a fifth variant embodiment.
Figure 9B:
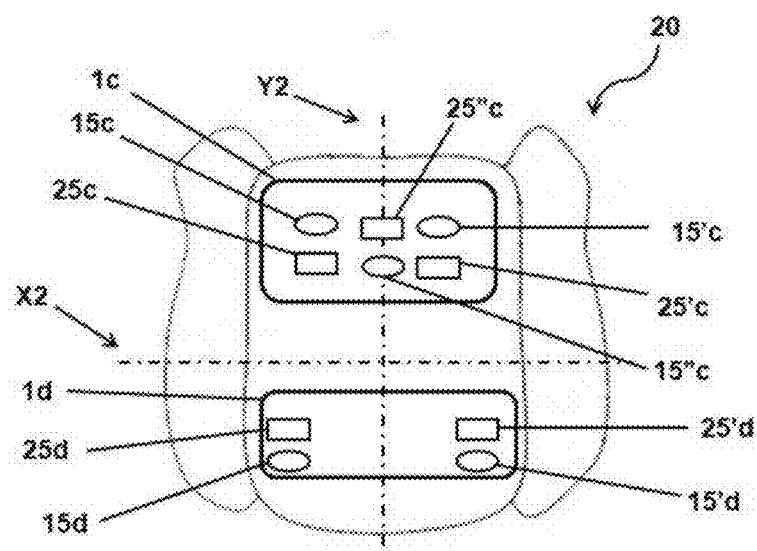
FIG. 9b shows an example of sensor positioning in a seating portion of a seat according to the fifth variant.

Reference is now made to FIGS. 9*a* and 9*b*, which represent a fifth alternative embodiment of sensor positioning, in the backrest in FIG. 9*a* and in the seating portion in FIG. 9*b*.

According to this fifth variant, the seat comprises a fifth measurement system providing a system combining several of the measurement systems described above, here an OCS classification system, an LF lumbar discomfort monitoring system, and a PD pelvic discomfort monitoring system.

This fifth measurement system comprises, in total, ten interdigital capacitive sensors 25*a*, 25'*a*, 25*b*, 25'*b*, 25"*b*, 25*c*, 25'*c*, 25"*c*, 25*d*, and 25'*d*, as well as ten resistive electrodes 15*a*, 15'*a*, 15*b*, 15'*b*, 15"*b*, 15*c*, 15'*c*, 15"*c*, 15*d*, and 15'*d*, providing a measurement system comprising four measurement areas with either two interdigital capacitive sensors and two resistive electrodes, or three interdigital capacitive sensors and three resistive electrodes, positioned in each area.

In FIG. 9*a*, sensors 25*a* and 25'*a* are positioned in the first measurement area 1*a*, one to each side of the vertical central plane Y1. Resistive electrode 15*a* is positioned near sensor 25*a* and resistive electrode 15'*a* is positioned near sensor 25'*a*. Resistive electrodes 15*a* and 15'*a* are positioned in the first measurement area 1*a* as well, one to each side of the vertical central plane Y1.

In addition, in FIG. 9*a*, sensors 25*b* and 25'*b* are positioned in the second measurement area 1*b*, one to each side of the vertical central plane Y1. Resistive electrode 15*b* is positioned near sensor 25*b* and resistive electrode 15'*b* is positioned near sensor 25'*b*. Resistive electrodes 15*b* and 15'*b* are positioned in the second measurement area 1*b* as well, one to each side of the vertical central plane Y1. Sensor 25"*b* and electrode 15"*b* are positioned close to each other in the second measurement area 1*b* and so as to be located along a line parallel to or within a parallel plane to the vertical central plane Y1, in other words approximately in the middle of the second measurement area 1*b*.

In FIG. 9*b*, sensors 25*c* and 25'*c* are positioned in the third measurement area 1*c*, one to each side of the longitudinal central plane Y2. Resistive electrode 15*c* is positioned near sensor 25*c* and resistive electrode 15'*c* is positioned near sensor 25'*c*. Resistive electrodes 15*c* and 15'*c* are positioned in the third measurement area 1*c* as well, one to each side of the longitudinal central plane Y2. Sensor 25"*c* and electrode 15"*c* are positioned close to each other in the third measurement area 1*c* and so as to be located along a line parallel to or within a plane parallel to the longitudinal central plane Y2, in other words approximately in the middle of the third measurement area 1*c*.

In addition, in FIG. 9*b*, sensors 25*d* and 25'*d* are positioned in the fourth measurement area 1*d*, one to each side of the longitudinal central plane Y2. Resistive electrode 15*d* is positioned near sensor 25d and resistive electrode 15'd is positioned near sensor 25'd. Resistive electrodes 15d and 15'd are positioned in the fourth measurement area 1d as well, one to each side of the longitudinal central plane Y2.

In one example, the number and positioning of the interdigital capacitive sensors and of the resistive electrodes for this fifth measurement system provide a system allowing both a classification of a seat occupant and a dynamic and personalized monitoring for the lumbar and pelvic pain that the occupant may be experiencing.

In these various exemplary embodiments, the interdigital capacitive sensor(s) is/are configured to provide a measurement comprised within the interval [300,3500] pF, where "pF" designates the unit of measurement for capacitance, expressed in picofarads.

In addition, in these various exemplary embodiments, the resistive electrode(s) is/are configured to provide a measurement within the interval [0, 300] $g/cm^2$, where "$g/cm^2$" denotes the unit of measurement for pressure, expressed in grams per square centimeter.

In one example, if at least one interdigital capacitive sensor is located in the first measurement area, it is suitable for measuring a capacitance within the interval [300,3500] pF. If at least one resistive electrode is located in the first measurement area, it is suitable for measuring a pressure within the interval [0, 30] $g/cm^2$.

In one example, if at least one interdigital capacitive sensor is located in the second measurement area, it is suitable for measuring a capacitance within the interval [300,2500] pF. If at least one resistive electrode is located in the second measurement area, it is suitable for measuring a pressure within the interval [30, 100]$g/cm^2$.

In one example, if at least one interdigital capacitive sensor is located in the third measurement area, it is suitable for measuring a capacitance within the interval [300,3500] pF. If at least one resistive electrode is located in the third measurement area, it is suitable for measuring a pressure within the interval [65, 300] $g/cm^2$.

In one example, if at least one interdigital capacitive sensor is located in the fourth measurement area, it is suitable for measuring a capacitance within the interval [300,2500] pF. If at least one resistive electrode is located in the fourth measurement area, it is suitable for measuring a pressure within the interval [10, 50] $g/cm^2$.

This makes it possible to take into account the physiology of a human user and the user's movements, since these measurement intervals are the ones that provide the best sensitivity for detecting a user occupying a seat.

The value of the capacitances and pressures measured at a given time allows directly obtaining information on the physiology of the user. For example, capacitance or pressure values measured as being close to zero in measurement areas 1a and 1d and low in measurement areas 1b and 1c may for example indicate that a small user is occupying the seat.

In a non-limiting manner, the seats and measurement systems described above may also be supplemented by other types of sensors such as ultrasonic sensors, induction sensors, radar sensors, or even LIDAR ("Light Detection And Ranging") sensors, their combination with at least one interdigital capacitive sensor and/or at least one resistive electrode making it possible to improve the precision, reliability, and plausibility of the measurements performed.

Figure 10:
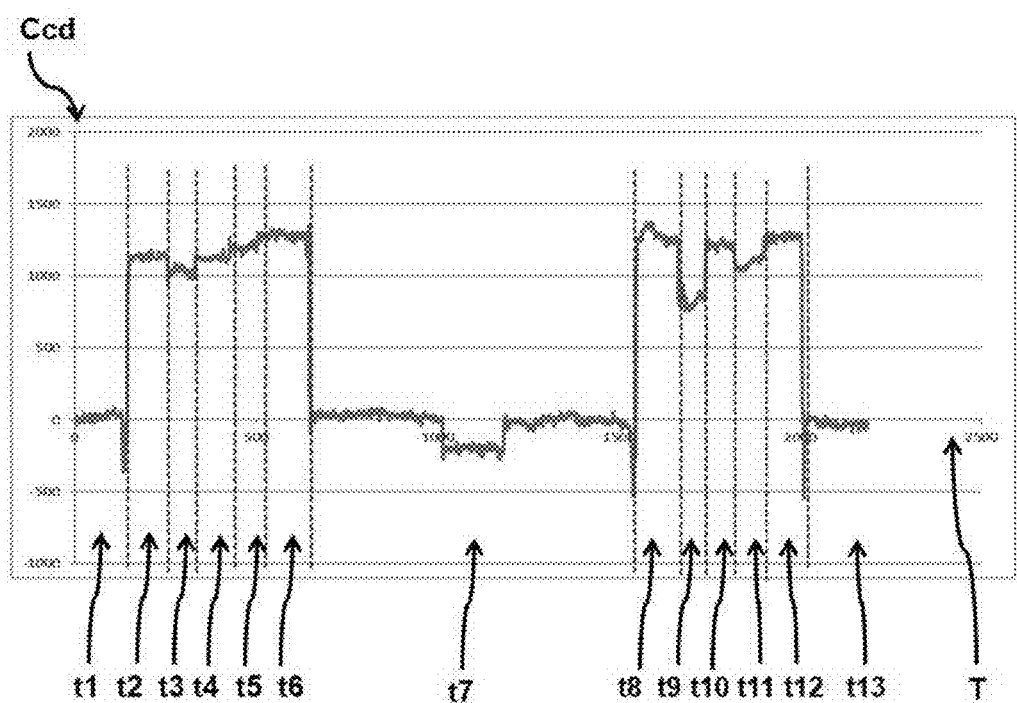
FIG. 10 shows an example of measurements from interdigital capacitive sensors located in a seating portion of a seat.

FIG. 10 represents a plurality of measurements made with several interdigital capacitive sensors located in a seating portion of a seat.

In particular, measurements of capacitance Ccd within the interval comprised between −1000 pF and 2000 pF are represented as a function of time T over thirteen time intervals t1 to t3 measured between 0 and 25 seconds. Here, these measurements are for example carried out by means of interdigital capacitive sensor 24c located in the third measurement area 1c and/or interdigital capacitive sensor 24d located in the fourth measurement area 1d, in the fourth variant embodiment. We thus obtain a capacitance measurement as a function of time and of the user seated on the seating portion of the seat.

These measurements illustrate the variability of the capacitances measured as a function of the presence of a user in the seat or of the user's movements relative to the seating portion of the seat, which can then be subsequently deduced by learning.

During time intervals t1, t7, and t13, no user is occupying the seat: the measured capacitance is thus close to 0 pF. Time intervals t2, t4, t6, t8, t10, and t12, with a measured capacitance close to 2500 pF, correspond to a normal sitting position of a same user in the seat. Time intervals t3, t5, t9, and t11, with a measured capacitance close to 1500 pF, correspond to a leaning-forward position of the user. Any variations are due, for example, to the user fidgeting or making small movements.

Thus, it is possible to discriminate between the cases of an unoccupied seat and of a user occupying the seat in the normal position or in a leaning position, with possible variations related to movements of the occupant. A similar measurement principle can be applied to the case of measurements carried out by means of interdigital capacitive sensors located in a seat backrest.

Figure 11:
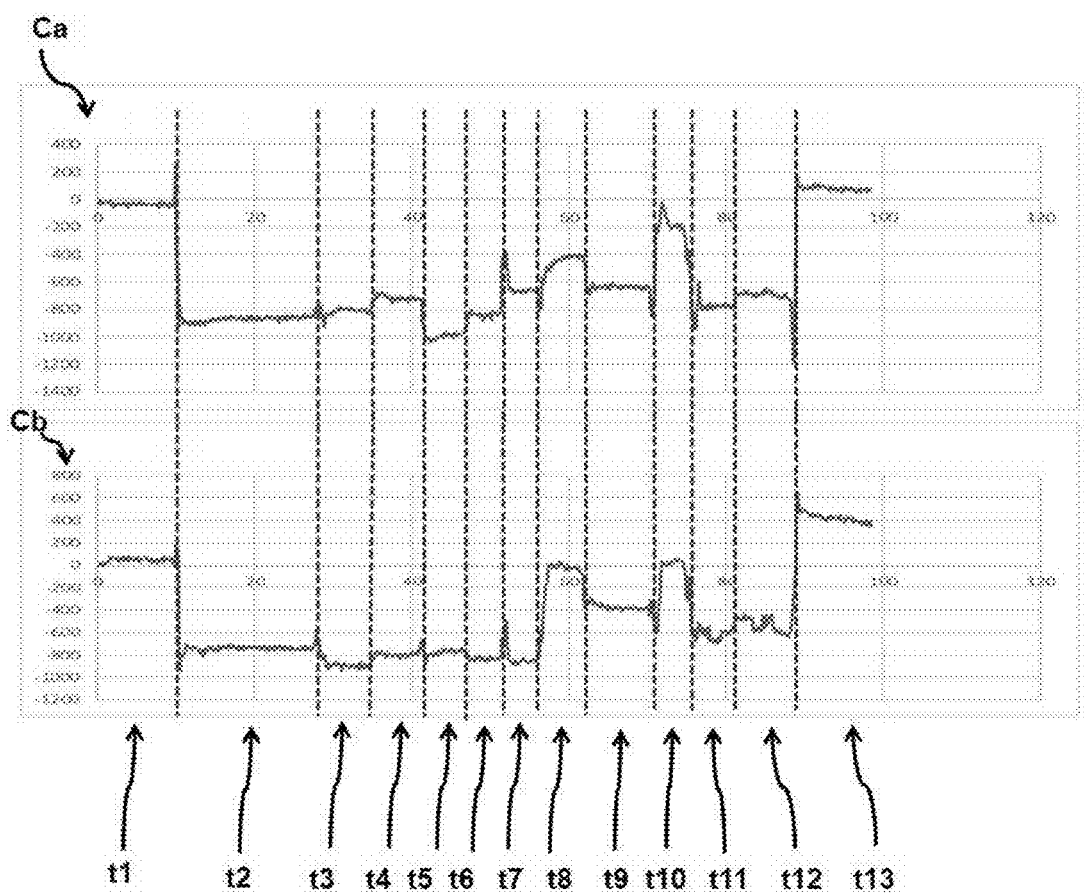
FIG. 11 shows an example of measurements from interdigital capacitive sensors located in two measurement areas of a backrest of the seat.

FIG. 11 shows a plurality of measurements made with interdigital capacitive sensors located in two separate measurement areas of a backrest of the seat.

In particular, capacitance measurements Ca by means of an interdigital capacitive sensor located in the first measurement area 1a, and capacitance measurements Cb by means of an interdigital capacitive sensor located in the second zone of measurement 1b, are carried out over a period of approximately 100 seconds.

The capacitance measurements made during time intervals t1 and t3 correspond to the situation where no user is occupying the seat. The capacitance measurements made during time intervals t2, t4, t6, t9, and t12 correspond to the situation where a user is occupying the seat in a normal position, and the capacitance measurements made during time intervals t3, t5, t7, t8, t10, and t11 correspond to the situation where a user is occupying the seat while fidgeting or making small movements.

These measurements illustrate the capacitances measured in two measurement areas of the seat backrest, as a function of the presence of a user in the seat or of the user's movements relative to the seating portion of the seat. The measured values and their variability according to the situation make it possible in particular to discriminate between the situations described above.

Figure 12:
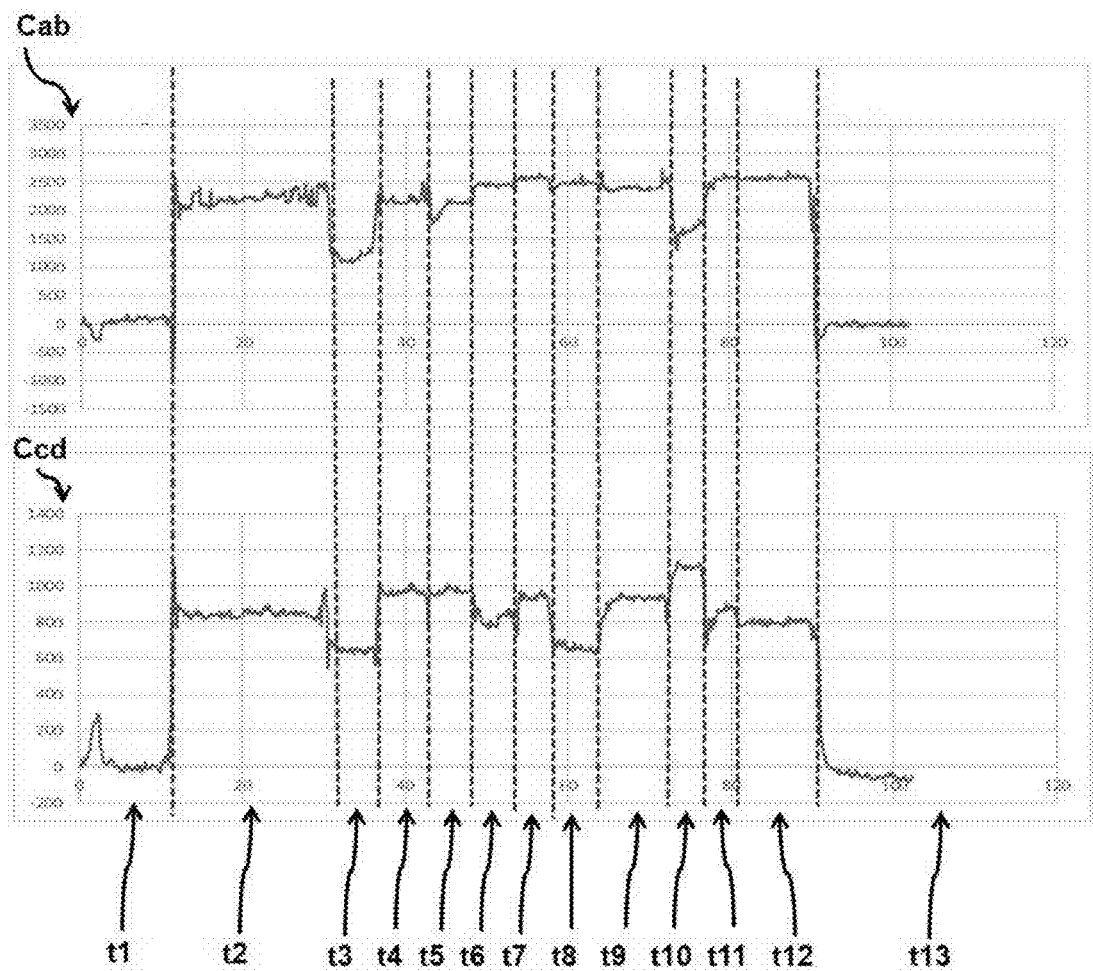
FIG. 12 shows an example of measurements from interdigital capacitive sensors located in two measurement areas of a seating portion of the seat.

FIG. 12 shows a plurality of measurements made with interdigital capacitive sensors located in two separate measurement areas of a seating portion of the seat.

In particular, capacitance measurements Cab resulting for example from averaging the measurements made by the interdigital capacitive sensors located in the first and second measurement areas, in other words in the backrest of the seat, and capacitance measurements Ccd resulting from averaging the measurements made by the interdigital capacitive sensors located in the third and fourth measurement areas, in other words in the seating portion of the seat, are carried out over a period of about 100 seconds.

As shown, the capacitance measurements made during time intervals t1 and t3 correspond to the situation where no user is occupying the seat. The capacitance measurements made during time intervals t2, t4, t6, t9, and t12 correspond to the situation where a same user is occupying the seat in a normal position, and the capacitance measurements made during time intervals t3, t5, t7, t8, t10, and t11 correspond to the situation where a user is occupying the seat while moving his or her right hand to in front of the chest.

This illustrates how the variation in values measured in the four distinct measurement areas 1a, 1b, 1c, and 1d makes it possible to discriminate between different situations.

For example, a large variation in a measured capacitance makes it possible to reveal a change in situation, for example to identify when a user moves from a normal position in the seat to one where he or she is suddenly pressing on a pedal with the right foot only.

By applying these principles in a general manner, it is also possible to monitor the movements of a user and to distinguish between situations where no user is occupying the seat, when a user is taking a seat, when he or she is moving the legs and/or torso and/or hips forward, backward, or to one side, when he or she is starting up the vehicle comprising the seat, when he or she is fastening a seat belt, when he or she is making adjustments to the seat, when he or she is seated in the normal position, when he or she is making foot movements for example pressing on a pedal, when he or she is moving the arms to manipulate a gear stick or sun visor or to turn a steering wheel, etc.

Along with measuring capacitances by means of interdigital capacitive sensors, the use of one or more resistive electrodes located in the seat allows providing pressure measurements which can be combined with the former to improve detection of these situations.

Figure 13:
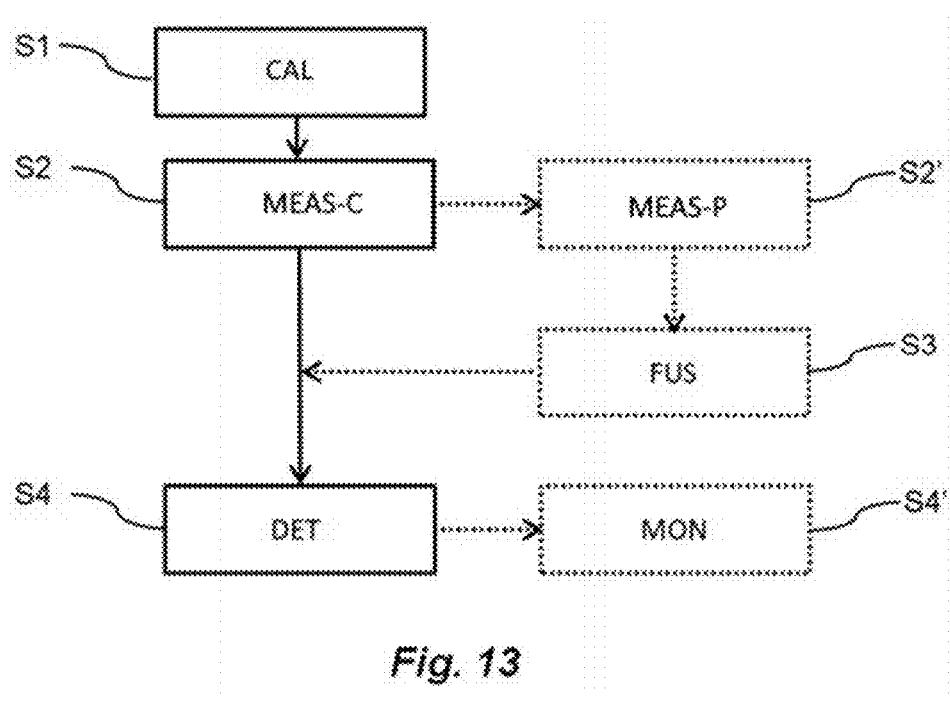
FIG. 13 shows an example of steps implemented by a measurement method according to various alternative embodiments.

Reference is now made to FIG. 13, which represents the steps implemented by a measurement method according to possible variant embodiments.

In the example presented here, the method is implemented by the seat 1 and by the controller 100 which is connected to one or more measurement areas of the seat in accordance with one of the variants described above. For example, the controller 100 is connected to areas 1a, 1b, 1c, and 1d and is configured to receive any measurement made by the interdigital capacitive sensors 25a, 25'a, 25b, 25'b, 25c, 25'c, 25d, and 25'd as well as by the resistive electrodes 15a, 15'a, 15b, 15'b, 15c, 15'c, 15d, and 15'd of the fifth embodiment of the seat.

As illustrated, the method comprises a step S1 implementing a calibration of each of these interdigital capacitive sensors. Typically, this calibration comprises a determination of an offset corresponding to a zero-load measurement carried out by this or these interdigital capacitive sensors, in other words carried out in the absence of any user in the seat. This zero-load measurement is then subtracted from the measurements subsequently made when a user is occupying the seat. Optionally, step S1 may also comprise calibration of the resistive electrodes.

The method further comprises a step S2 of making use of interdigital capacitive sensors to acquire capacitance values, from which a plurality of displacements or movements of the user occupying the seat can be deduced. This can be done at regular intervals, automatically or on request, for example when the user presses against one of the sensors after a specified period of time.

Simultaneously with or successively to step S2, an optional step S2' of the method may make use of one or more resistive electrodes of the at least one measurement area to which the controller 100 is connected, to acquire pressure values, in particular of pressures exerted by one or more parts of the user's body when the user is occupying the seat.

Simultaneously with or successively to step S2, an optional step S3 of the method may make use of the controller 100 to fuse the measurements made. This makes it possible to deduce a set of fused measurements combining pressure measurements and capacitance measurements, from which it is possible to deduce, at a same corresponding measurement time, a specific position or situation of the user as a function of the distance or movement and pressure that were determined.

Successively to step S2 and/or step S3, a step S4 of the method makes use of the controller 100 to detect the user or to determine the type of user based on a comparison between the distances, movements, and/or pressures determined in accordance with the preceding steps.

Simultaneously with or successively to step S4, an optional step S4' of the method may make use of the controller 100 to monitor for lumbar pain of the user and/or pelvic pain of the user, this monitoring being based on an average and/or a gradient of several of the determined distances or movements, or possibly of determined pressures.

At any time during a given measurement, the controller 100 may store the previous measurements in a memory in order to compare them to new measurements.

In particular, an average of several pressure and/or capacitance measurements can serve as a basis for identifying significant deviations at a given moment, for example if the user adopts a different position than usual due to back pain.

Similarly, a gradient corresponding to the instantaneous slope of at least two measurements of pressure and/or capacitance can serve as a basis for identifying sudden variations in their evolution over time, for example if the user tilts his or her body forward in order to open a door of the vehicle comprising the seat.

Figure 14:
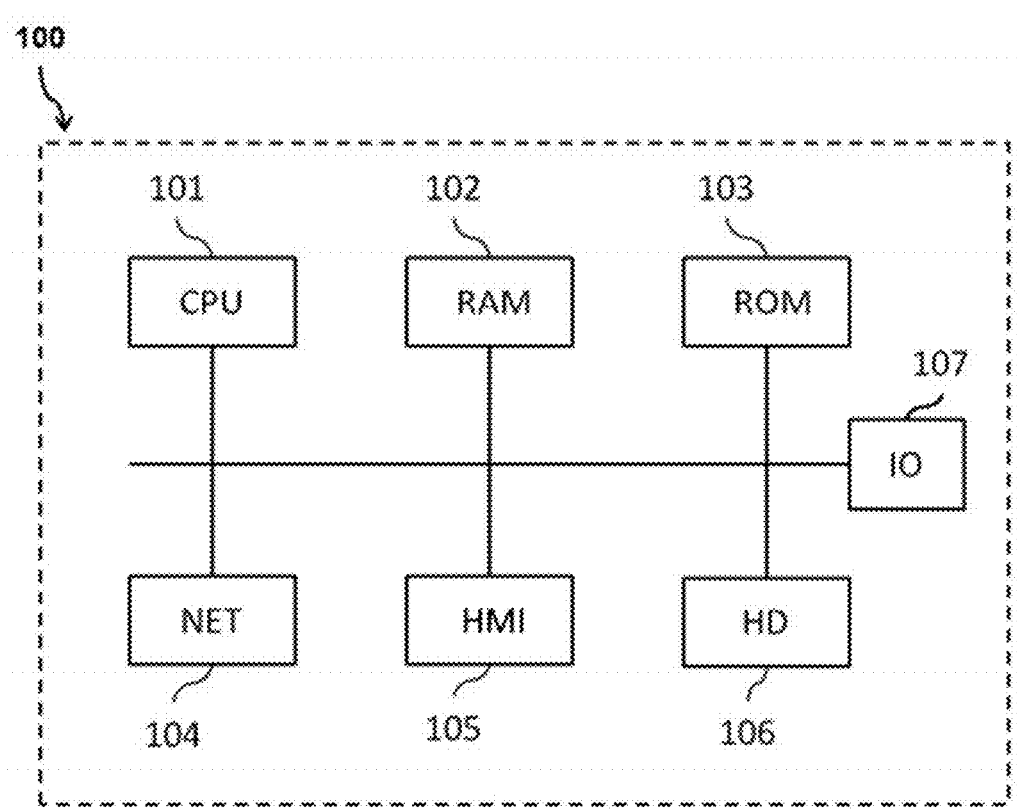
FIG. 14 shows an example of a schematic block diagram of a controller.

FIG. 14 represents an example of a schematic block diagram of a controller according to one example implementation.

In a non-limiting manner, the controller 100 comprises a communication bus, connected for example to a central processing unit 101 such as a processor or a microprocessor and denoted CPU.

The controller 100 also comprises a random access memory 102, denoted RAM, in particular for storing executable code of a measurement method.

Preferably, this executable code makes it possible to implement a measurement method by means of the sensors in accordance with the exemplary embodiments described above.

In one example, anthropometric positioning of resistive electrodes and interdigital capacitive sensors, preferably combined with data fusion, makes it possible to evaluate, detect, and classify different physiologies and situations or positions of a user occupying a seat, continuously and reliably.

In one example, the executable code makes it possible to configure the controller 100 to perform noise filtering and processing of the signal of measurements that are received, for example to extract unprocessed measurements such as the dielectric variation.

In one example, the controller 100 also comprises registers suitable for storing the variables and parameters necessary for implementing such a method. The memory capacity of the controller 100 may be supplemented with an optional RAM memory connected to an expansion slot, for example.

In addition, the controller 100 comprises read-only memory 103, denoted ROM, for storing computer programs for implementing the embodiments, as well as a network interface 104 which is normally connected to a communication network on which digital data to be processed are transmitted or received.

The network interface 104 may be a single network interface, or composed of a set of different network interfaces (for example wired and wireless, interfaces or different types of interfaces that are wired or wireless).

Data packets are sent over the network interface for transmission or are read from the network interface for reception, under the control of the software application running in the processor or microprocessor 101.

Furthermore, the controller 100 comprises a user interface 105 for receiving inputs from a user or for displaying information to a user, an optional storage medium 106 denoted HD, and an input-output module 107 denoted IO, for receiving/sending data from or to external devices such as a hard drive, a removable storage medium, or the like.

In an example presented here, the executable code may be stored in read-only memory 103, in the storage medium 106, or in a removable digital medium such as a disk for example.

According to one variant, the executable code of the programs may be received by means of a communication network, via the network interface 104, in order to be stored in the storage medium 36 before being executed.

In one example, the controller 100 is equipped with one or more memories comprising and capable of executing one or more programs.

The central processing unit 101 is suitable for controlling and directing the execution of instructions or portions of software code of the program or programs according to one of the embodiments, instructions which are stored in one of the storage means mentioned above. After power-up, the CPU 101 is able to execute instructions stored in the main RAM memory 102, relating to a software application, after these instructions have been loaded from ROM for example.

In the example shown here, the controller 100 is a programmable device that uses software. However, in the alternative, the present disclosure may be implemented in any type of hardware (for example, in the form of a dedicated integrated circuit or ASIC).

The controller 100 is arranged to be connected to a measurement system comprising one or more of the sensors described above. In addition, the controller 100 is arranged to be connected to one measurement sheet 50 or several measurement sheets 50, 50' as described above.

In one example, a sheet as previously described comprises the controller 100. Alternatively, a third-party device configured as a measurement system comprises the controller 100.

In other examples, the controller 100 is integrated into the seat or into other elements of a vehicle which comprises the seat, for example a dashboard of a vehicle or even into one of the capacitive sensors described above.

According to one example, the controller 100 is an engine control unit, i.e. an ECU.

According to one example, the controller 100 is connected to or is comprised in an ECU.

In one example, an ECU is configured to control the operation of one or more actuators in a vehicle. Such an ECU needs data from sensors to measure parameters such as temperature, pressure, etc. Such an ECU also needs software or algorithms to control the parameters of such actuator(s), for example an airbag of the vehicle, an accelerator or brake pedal of the vehicle, etc.

In the specific examples of the present disclosure, an ECU serving as a controller 100 may also be configured for obtaining and processing measurements from the interdigital capacitive sensor(s) of the seat and/or measurements from one or more resistive electrode(s) of the seat.

Furthermore, the ECU serving as a controller 100 may also be configured to combine these measurements with other data supplied to it, for example to more accurately determine a physiology of a user occupying the seat or to implement an operation on the basis of a determined physiology.

For example, an algorithm used by an ECU may use the measurements made by five interdigital capacitive sensors and five resistive electrodes comprised in the seat 1 to which the ECU is connected. Upon receiving these measurements, the ECU applies signal processing to these measurements, conditions them, and then deduces a weight, a height, and more generally a physiology of a user occupying the seat at the time the measurements are made.

To detect an occupant of a vehicle seat or to determine the physiology of that occupant, a measurement sequence is implemented. For example, such a measurement sequence is started by the controller 100 when a user sits down on the seat at time To.

Initial detection measurements for the user are made, for example an estimate of a weight, height, or position of this user in the seat, and a corresponding state of the user is transmitted to the controller 100 at $T_0+0.1$ seconds, at $T_0+0.25$ seconds, or at $T_0+0.5$ seconds.

In one example, the response time of the system for its complete implementation is less than 1 second.

The system then monitors the position and state of the seat occupant during operation of the vehicle by collecting the measurements made by the sensors connected to the controller 100.

According to various examples, the controller 100 comprises one or more programs configured to implement various actions such as those described below.

In particular, the controller 100 comprises a data fusion algorithm which allows combining the capacitance measurements coming from one or more interdigital capacitive sensors and from one or more resistive electrodes located in the seat, in order to provide a detection of a user in the seat, a classification of the type of user, and/or to monitor his or her body movements in relation to the backrest and/or seating portion. This fusion may be carried out in a cooperative, competitive, or complementary manner.

An example of a program implemented by controller 100 is a program configured to estimate a weight and/or height of a user occupying the seat.

Another example of a program implemented by the controller 100 is a program configured to determine a position or a type of position of a user occupying the seat, for example on the basis of: movements of the user's legs, brief presses against the backrest or seating portion of the seat, repositioning or twisting of the user's back against the backrest, sagging of the shoulders, fidgeting or other changes in posture that could lead to a suspicion of fatigue, fighting against falling asleep, or even a decrease in attention.

This program may also be configured to identify in which direction the user is facing in general, for example towards the front of the vehicle if the user is driving the vehicle on a road, towards the sides of the vehicle if the user is performing a maneuver, or towards the rear of the vehicle if backing up.

As an example, it is possible to determine if and when the user is leaning forward with one or more arms resting on the dashboard or on the steering wheel of the vehicle, to the side with one hand raised above the head to adjust a rear view mirror or sun visor, to the side with one hand below chest level to manipulate a gear stick or a navigation system of the vehicle, etc.

This program may also be configured to identify an action performed or about to be performed by an occupant of the seat, for example if the occupant is leaning his or her weight on a specific side of the seat because he or she is getting ready to open a vehicle door, or if he or she is getting up from the seat to move to another seat in the vehicle.

Yet another example of a program implemented by the controller 100 is a program configured to determine a type of user occupying the seat, for example depending on whether that user is an adult or a child. This program also allows determining whether the seat is occupied by a human being, an object, etc.

Detecting, classifying, and tracking the movements of a user occupying a vehicle seat, and in particular an occupant of a motor vehicle seat, whether a driver or a passenger may be beneficial.

This beneficial use is significant in the context of designing seat occupant detection systems intended to be produced for the general public and based on the use of sensors integrated into these seats in order to allow monitoring the drivers and passengers of vehicles.

This is particularly true for monitoring the users of autonomous vehicles, which requires a conditional level of automation in which the driving of the vehicle is delegated in predefined situations.

In these various contexts, there are comparative systems for monitoring users occupying vehicle seats. These comparative systems use sensors arranged to measure physical and physiological attributes of people present in the vehicle. For example, a car driver's fatigue level can be monitored using a camera, a passenger's position can be monitored using a motion sensor located above the seat, etc.

However, the measurements obtained by such comparative devices are obtained with a generally high response time of several seconds, which is unsuitable for providing data sufficiently quickly in certain situations, particularly in the event of an accident.

For example, adapting the properties of an airbag device intended to protect a user occupying a vehicle seat, in the event of an accident may be beneficial. The operation of comparative devices could thus be improved by adjusting the properties of an airbag and/or of a seat belt pretensioner of a vehicle seat on the basis of real-time knowledge of parameters such as the exact position of the user in the seat, type of user, height, weight, etc.

In addition, the measurements obtained by such comparative devices are generally imprecise and do not allow knowing how a user and the limbs of that user are positioned relative to the various component elements of a seat.

For example, there may be a benefit to warn a user of a vehicle seat that his or her posture is not suitable for long-term occupation of the seat, and that it would be beneficial for the user to adjust the relative position of the backrest in relation to the seating portion or to the armrests, in order to avoid back pain in particular.

In addition, the measurements obtained by such comparative devices often lack robustness because they have little tolerance for significant disruptions or low-intensity disruptions which could affect them.

For example, there may be a benefit to detecting a signal resulting from slight movements such as the jiggling of a user occupying the seat that are due to the user's own movements and are not influenced by vibrations specific to the vehicle in which he or she is seated, the vibrations of the vehicle generating interference relative to the signal corresponding to measurements carried out under normal conditions.

In response to the aforementioned disadvantages as well as to this or these benefits, the present description relates primarily to a seat comprising: a backrest; a seating portion connected to the backrest; and at least one measurement area defined on the backrest and/or on the seating portion, the at least one measurement area comprising at least one interdigital capacitive sensor capable of measuring a distance or a movement of a user occupying the seat.

This makes it possible to provide a device capable of making anthropometric measurements of a user occupying the seat, which have the advantage of being more ergonomic than traditional measurements.

In this document, anthropometric measurements are measurements of dimensional features of an individual, including height, chest height, lengths of limbs such as arms and legs, the person's mass or the mass of the limbs, or the corresponding centers of gravity. It is thus possible to define one or more user classifications, for example according to their gender, or according to their weight in order to distinguish a child from an adult by whether the mass of the user is greater than 25 kilograms or less than 70 kilograms, for example.

In this document, an interdigital capacitive sensor is a sensor comprising at least one electrode which allows detecting a variation in distance, this distance possibly being very small, based on the capacitive effect. By virtue of this capacitive effect, a determination of the distance is obtained by measuring the capacitance of the capacitor, this capacitance being inversely proportional to the distance to be measured and proportional to the product of the surface area of the sensor electrode and the permittivity of the dielectric existing between the sensor and the part to be measured. As a result, there is a direct relation between the value of a measured capacitance and the value of a corresponding distance or movement.

Herein, a measurement area is a surface area of the backrest and/or of the seating portion, or more generally of the seat, inside of which at least one interdigital capacitive sensor has sufficient sensitivity to detect a variation of the distance or of the movement.

Herein, an interdigital sensor, and in particular an interdigital capacitive sensor, is a sensor formed of at least one plate or of at least one metal electrode arranged in the shape of a comb, and preferably having two faces opposite to each other.

In one example, an interdigital capacitive sensor makes it possible to provide a sensor of reduced volume but which has a maximized useful surface area, which increases the capacitance and sensitivity of the sensor while reducing its thickness.

In one example, an interdigital capacitive sensor also allows obtaining measurements over short time intervals of about a microsecond. This makes it possible to provide a fast, precise system with high plausibility.

According to one specific example, the at least one measurement area further comprises at least one resistive electrode capable of measuring a contact pressure of a user occupying the seat.

This makes it possible to provide a multiphysical single-technology device for monitoring the weight and/or the contact force exerted by a user on a surface of the seat, in particular the seating portion and/or the backrest of the seat.

In addition, the combination of at least one interdigital capacitive sensor with at least one resistive electrode makes it possible to achieve optimum sensitivity for detecting a user and/or classifying a type of user occupying the seat. This combination also allows increasing the plausibility and reliability of the data in a manner that is greatly superior in terms of their possible redundancy.

In general, the use of two such different types of sensors also allows strengthening the on-board diagnostic capabilities of a vehicle, known as OBD capabilities, and the plausibility of the measurements, by using their complementarity as well as their redundancy.

Herein, a resistive electrode is any type of resistive sensor capable of measuring a pressure in the at least one measurement area of the seating portion and/or of the backrest of the seat, for example based on a variation in the resistivity of this element.

Herein, "$g/cm^2$" indicates the unit of measurement for pressure expressed in grams per square centimeter, and such that 1 $g/cm^2$ is equal to 98.0665 Pa in the international system of units, where "1 Pa" denotes 1 Pascal.

Herein, the maximum pressure generally applied by a user to a seating portion of a seat is about 90 $g/cm^2$, and the maximum pressure generally applied to a seat backrest is 70 $g/cm^2$.

According to one specific example, the seat further comprises at least one measurement sheet forming the at least one measurement area and electrically connecting the at least one interdigital capacitive sensor to the at least one resistive electrode.

The measurement sheet thus makes it possible to connect a plurality of interdigital capacitive sensors and resistive electrodes.

According to one specific example, all the interdigital capacitive sensors and resistive electrodes formed by a measurement sheet are electrically connected to one another.

This makes it possible to simplify the manufacture of seats comprising the measurement areas, for example when the sheet is manufactured on a substrate.

According to one specific example, at least one distance separating the at least one interdigital capacitive sensor and the at least one resistive electrode is less than 50 millimeters and greater than 10 millimeters, preferably equal to 20 millimeters.

Herein, an accuracy of plus or minus 2.5 millimeters is considered for determining a distance between two elements.

Positioning an interdigital capacitive sensor and a resistive electrode in such proximity to one another advantageously increases the accuracy and reliability of the measurements obtained by their combination. The combination of these measurements is optimal when the distance between each interdigital capacitive sensor-resistive electrode pair is 20 millimeters plus or minus 2.5 millimeters.

According to one specific example, the total number of interdigital capacitive sensors comprised in the seat is strictly greater than one and strictly less than six, preferably equal to four, and the total number of resistive electrodes comprised in the seat is strictly greater than one and strictly less than six, preferably equal to four.

According to one specific example, the seat comprises four measurement areas, the first and second of the measurement areas being formed on the backrest and one to each side of a horizontal central plane of the backrest, the third and fourth of the measurement areas being formed on the seating portion and one to each side of a transverse central plane of the seating portion.

According to one specific example:
the first measurement area comprises an interdigital capacitive sensor and a resistive electrode which are located on a same side of a vertical central plane of the backrest; the third measurement area comprises an interdigital capacitive sensor and a resistive electrode which are located substantially along a longitudinal central plane of the seating portion; and
the second measurement area comprises an interdigital capacitive sensor and a resistive electrode which are located substantially along the vertical central plane;
the third measurement area comprises an interdigital capacitive sensor and a resistive electrode which are located substantially along a longitudinal central plane of the seating portion; and
the fourth measurement area comprises an interdigital capacitive sensor and a resistive electrode which are located on a same side of the longitudinal central plane.

This makes it possible to provide a measurement system which is a seat occupant detection system exhibiting a high reliability, called the ODS system.

Herein, an element, here an interdigital capacitive sensor or a resistive electrode, being located substantially along a given plane means that this element is partially located within this given plane or is distanced from it by a distance less than or equal to 5 centimeters.

In one example, in this specific example, the vertical central plane of the backrest and the longitudinal central plane of the seating portion are identical and define one and the same plane, called the plane of symmetry of the seat, which is generally the case when the backrest and the seating portion are aligned.

Still according to this specific example, and when the vertical central plane of the backrest and the longitudinal central plane of the seating portion are identical and define the plane of symmetry of the seat, the interdigital capacitive sensor comprised in the first measurement area and the interdigital capacitive sensor comprised in the fourth measurement area are located on opposite sides of the seat's plane of symmetry; furthermore, the resistive electrode comprised in the first measurement area and the resistive electrode comprised in the fourth measurement area are located on opposite sides of the seat's plane of symmetry.

In one example, the examples of a seat for which at least two interdigital capacitive sensors and/or at least two resistive electrodes are located in the same measurement area, or even in separate measurement areas, allow making differential measurements.

This makes it possible to increase robustness by filtering or eliminating specific measurements: for example, one can use a particular selection of at least two interdigital capacitive sensors and/or resistive electrodes to highlight measurements due to movements or vibrations that are slight and therefore more difficult to measure, or conversely to eliminate them and thus improve the signal-to-noise ratio.

For example, the implementation of differential measurements by means of a plurality of interdigital capacitive sensors and/or resistive electrodes makes it possible to detect fidgeting movements of a user occupying the seat, or the user turning his or her head to look behind, etc.

According to one specific example:
the first measurement area comprises, on each side of a vertical central plane of the backrest, an interdigital capacitive sensor and a resistive electrode;
the second measurement area comprises an interdigital capacitive sensor and a resistive electrode which are located substantially along the vertical central plane;
the third measurement area comprises an interdigital capacitive sensor and a resistive electrode which are located substantially along a longitudinal central plane of the seating portion; and
the fourth measurement area comprises, on each side of the longitudinal central plane, an interdigital capacitive sensor and a resistive electrode.

This makes it possible to provide a measurement system which is an occupant classification system, called the OCS system. Such an OCS system allows determining the type of user occupying the seat, for example an adult, a child, a male user, a female user, etc.

According to one specific example:
the first measurement area comprises an interdigital capacitive sensor and a resistive electrode which are located substantially along a vertical central plane of the backrest;
the second measurement area comprises, on each side of the vertical central plane, an interdigital capacitive sensor and a resistive electrode;
the third measurement area comprises an interdigital capacitive sensor and a resistive electrode which are located substantially along a longitudinal central plane of the seating portion; and
the fourth measurement area comprises, on each side of the longitudinal central plane, an interdigital capacitive sensor and a resistive electrode.

This makes it possible to provide a measurement system which is a lumbar discomfort monitoring system, called the LF system (or "Lumbar Fit"). Such an LF system allows detecting back pain experienced by a user occupying the seat, particularly in the lumbar region, for example due to poor positioning of the user in the seat or poor adjustment of the backrest and/or seating portion of the seat.

It is thus possible to provide the user with a signal or information enabling the user to react, for example to avoid pinched vertebrae and, in the longer term, back pain.

According to one specific example:
the first measurement area comprises an interdigital capacitive sensor and a resistive electrode which are located substantially along a vertical central plane of the backrest;
the second measurement area comprises an interdigital capacitive sensor and a resistive electrode which are located substantially along the vertical central plane;
the third measurement area comprises, on each side of a longitudinal central plane of the seating portion, an interdigital capacitive sensor and a resistive electrode; and
the fourth measurement area comprises, on each side of the longitudinal central plane, an interdigital capacitive sensor and a resistive electrode.

This makes it possible to provide a measurement system which is a pelvic discomfort monitoring system, known as the PD system (for "Pelvis Drift"). Such a PD system makes it possible to detect any pelvic pain experienced by a user occupying the seat, in particular in the region of the pelvis, the pelvic area, including the lower abdomen and the genital area, for example due to poor positioning of the user in the seat or poor adjustment of the backrest and/or seating portion of the seat.

It is thus possible to provide the user with a signal or information enabling the user to react, for example to avoid pinching in the legs or hips.

According to one specific example:
the first measurement area comprises, on each side of a vertical central plane of the backrest, an interdigital capacitive sensor and a resistive electrode;
the second measurement area comprises, on each side of the vertical central plane, an interdigital capacitive sensor and a resistive electrode, the second measurement area further comprising an interdigital capacitive sensor and a resistive electrode along the vertical central plane;
the third measurement area comprises, on each side of a longitudinal central plane of the seating portion, an interdigital capacitive sensor and a resistive electrode, the third measurement area further comprising an interdigital capacitive sensor and a resistive electrode along the longitudinal central plane; and
the fourth measurement area comprises, on each side of the longitudinal central plane, an interdigital capacitive sensor and a resistive electrode.

This makes it possible to provide a measurement system that combines several types of measurement systems, namely an OCS classification system, an LF lumbar discomfort monitoring system, and a PD pelvic discomfort monitoring system. This thus allows determining a classification of a user occupying the seat while monitoring for possible lumbar pain and pelvic pain in the user.

In one example, the positioning of the interdigital capacitive sensors and resistive electrodes in the measurement systems mentioned above makes it possible to provide an anthropometric device, meaning capable of detecting and identifying the majority of the physiologies and positions permitted by a seat user.

According to one specific example, at least one interdigital capacitive sensor is suitable for measuring a capacitance greater than 300 picofarads and less than 3500 picofarads, preferably less than 2500 picofarads if the at least one interdigital capacitive sensor is located in the second measurement area or in the fourth measurement area; and at least one resistive electrode is suitable for measuring a pressure of less than 300 g/cm$^2$, preferably less than 30 g/cm$^2$ if the resistive electrode is located in the first measurement area, preferably greater than 30 g/cm$^2$ and less than 100 g/cm$^2$ if the resistive electrode is located in the second measurement area, preferably greater than 65 g/cm$^2$ if the resistive electrode is located in the third measurement area, preferably greater than 10 g/cm$^2$ and less than 50 g/cm$^2$ if the resistive electrode is located in the fourth measurement area.

Herein, "pF" indicates the unit of measurement for capacitance, expressed in picofarads.

This makes it possible to provide capacitance measurements and pressure measurements with a sensitivity that takes into account human physiology, and in particular, an optimal sensitivity for implementing the detection of a human user in the seat, the determination of a type of seat occupant, and the monitoring for lumbar pain and/or pelvic pain of a human user in the seat.

Secondly, the present application relates to a controller arranged so as to be connected to the at least one measurement area of a seat according to any one of the preceding specific examples, the controller being configured for determining a type of user occupying the seat, detecting the user, monitoring for lumbar pain of the user and/or monitoring for pelvic pain of the user.

According to one specific example, the controller comprises computer means, for example hardware comprising a processor, a microprocessor, or a board of sensors, the hardware being arranged to implement a computer program such as software or an algorithm.

Herein, the software or algorithm uses an intelligent method of data fusion, based on measurements made by at least one interdigital capacitive sensor and at least one resistive electrode, preferably located near one another.

Such processing of these data makes it possible, from these measurements, to evaluate and provide an accurate detection of a user occupying the seat and to classify the type of user.

In particular, this software or algorithm comprises instructions for implementing a detection of an occupant in the seat when the measurement system comprising the at least one measurement area is an ODS system, when the instructions are executed by the controller hardware.

Additionally or alternatively, this software or algorithm comprises instructions for implementing a classification of an occupant in the seat when the measurement system comprising the at least one measurement area is an OCS system, when the instructions are executed by the controller hardware.

Additionally or alternatively, this software or algorithm comprises instructions for implementing a lumbar discomfort monitoring of an occupant in the seat when the measurement system comprising the at least one measurement area is an LF system, and when the instructions are executed by the controller hardware.

Additionally or alternatively, this software or algorithm comprises instructions for implementing a pelvic discomfort monitoring of an occupant in the seat when the measurement system comprising the at least one measurement area is a PD system, and when the instructions are executed by the controller hardware.

In one specific example, the controller is an engine control unit which is external to the seat.

Herein, an engine control unit, or ECU, is a control unit configured to receive data coming from sensors of any type arranged in the vehicle, and in the present case, interdigital capacitive sensors and resistive electrodes comprised in the at least one measurement area to which the controller is arranged to be connected.

Herein, in addition, an ECU may adapt or modify parameters of the engine or of the vehicle in general, for example engine torque, cruise control, automatic gear shifting, emission control, fuel distribution, or the ignition timing of the vehicle's engine. An ECU may also adapt or modify parameters of the parameters of other devices installed in the vehicle, for example a loudspeaker, an airbag, a camera, an air conditioning system, etc.

The present application relates thirdly to a measurement system, the measurement system comprising a seat according to any one of the preceding specific examples and a controller according to any one of the preceding specific examples.

In one example, the seats, the controllers, and the measurement systems to which the present application relates have high ergonomics and can be produced at a reduced cost for large-scale distribution.

The present application relates fourthly to a measurement method implemented by means of a seat comprising a backrest, a seating portion connected to the backrest, at least one measurement area defined on the backrest and/or on the seating portion, the at least one measurement area comprising at least one interdigital capacitive sensor capable of measuring a distance or movement of a user occupying the seat, the at least one measurement area of the seat being connected to a controller configured for determining a type of user occupying the seat or for detecting the user, the method comprising:
 calibrating the at least one interdigital capacitive sensor by performing a measurement when the seat is not occupied;
 determining, with the at least one calibrated interdigital capacitive sensor, a plurality of distances or movements of the user when the user is occupying the seat; and
 detecting the user or determining the type of user, based on a comparison between several of the determined distances or movements.

Herein, and in a non-limiting manner, the plurality of distances or movements may be determined by a same sensor or by several same sensors at different given times. The plurality of distances or movements may also be determined by several sensors at the same time. The plurality of distances or movements may also be determined by several sensors at several times.

This provides a quantitative means of detecting a user in a seat or of determining a type of user occupying the seat.

In one specific example, the at least one measurement area further comprises at least one resistive electrode capable of measuring a contact pressure of a user occupying the seat, the method further comprising:
 determining, with the at least one calibrated resistive electrode, a plurality of contact pressures of the user; and fusing several of the determined contact pressures with several of the determined distances or movements in order to form a set of fused measurements,
 fusing several of the determined contact pressures with several of the determined distances or movements in order to form a set of fused measurements,
 the user detection or the user type determination being implemented based on a comparison between several of the fused measurements.

This improves the accuracy and reliability of the detection of a user in the seat or the determination of the user type, by combining several types of measurements.

In another specific example, the controller is further configured to monitor for lumbar pain of the user and/or pelvic pain of the user, the method further comprising:
 monitoring for lumbar pain and/or pelvic pain of the user based on an average and/or a gradient of several of the determined distances or movements.

Herein, a gradient is equivalent to a slope or a derivative of the evolution over time of the determined distances or movements.

Herein, the monitoring for lumbar pain and/or pelvic pain of the user may also be done on the basis of an average and/or gradient of determined pressures.

This makes it possible to improve the reliability of a monitoring for pelvic and/or lumbar discomfort in a user occupying the seat, based on variations in the measurements made.

Seat (1) comprising: —a backrest (10); —a seating portion (20) connected to the backrest; and —at least one measurement area (1a, 1b, 1c, 1d) defined on the backrest and/or on the seating portion, the at least one measurement area comprising at least one interdigital capacitive sensor (20a) capable of measuring a distance or a movement of a user occupying the seat.

The following numbered clauses include embodiments that are contemplated and non-limiting:

Clause 1. A seat (1) comprising:
a backrest (10);
a seating portion (20) connected to the backrest; and
at least one measurement area (1a, 1b, 1c, 1d) defined on the backrest and/or on the seating portion, the at least one measurement area comprising at least one interdigital capacitive sensor capable of measuring a distance or a movement of a user occupying the seat.

Clause 2. The seat according to clause 1, wherein the at least one measurement area further comprises at least one resistive electrode capable of measuring a contact pressure of a user occupying the seat.

Clause 3. The seat according to clause 2, further comprising at least one measurement sheet (50; 50a, 50b) forming the at least one measurement area and electrically connecting the at least one interdigital capacitive sensor to the at least one resistive electrode.

Clause 4. The seat according to clause 3, any other suitable clause, or combination of suitable clauses, wherein at least one distance separating the at least one interdigital capacitive sensor and the at least one resistive electrode is less than 50 millimeters and greater than 10 millimeters, preferably equal to 20 millimeters.

Clause 5. The seat according to clauses 2 to 3, wherein the total number of interdigital capacitive sensors comprised in the seat is strictly greater than one and strictly less than six, preferably equal to four, and wherein the total number of resistive electrodes comprised in the seat is strictly greater than one and strictly less than six, preferably equal to four.

Clause 6. The seat according to any one of the preceding clauses, wherein the seat comprises four measurement areas, the first (1a) and second (1b) of the measurement areas being formed on the backrest and one to each side of a horizontal central plane (X1) of the backrest, the third (1c) and fourth (1d) of the measurement areas being formed on the seating portion and one to each side of a transverse central plane (X2) of the seating portion.

Clause 7. The seat according to clause 6, wherein:
the first measurement area (1a) comprises an interdigital capacitive sensor (21a) and a resistive electrode (11a) which are located on a same side of a vertical central plane (Y1) of the backrest;
the second measurement area (1b) comprises an interdigital capacitive sensor (21b) and a resistive electrode (11b) which are located substantially along the vertical central plane (Y1);
the third measurement area (1c) comprises an interdigital capacitive sensor (21c) and a resistive electrode (11c) which are located substantially along a longitudinal central plane (Y2) of the seating portion; and
the fourth measurement area (1d) comprises an interdigital capacitive sensor (21d) and a resistive electrode (11d) which are located on a same side of the longitudinal central plane (Y2).

Clause 8. The seat according to clause 6, wherein:
the first measurement area (1a) comprises, on each side of a vertical central plane (Y1) of the backrest, an interdigital capacitive sensor (22a, 22'a) and a resistive electrode (12a, 12'a);
the second measurement area (1b) comprises an interdigital capacitive sensor (22b) and a resistive electrode (12b) which are located substantially along the vertical central plane (Y1);
the third measurement area (1c) comprises an interdigital capacitive sensor (22c) and a resistive electrode (12c) which are located substantially along a longitudinal central plane (Y2) of the seating portion; and
the fourth measurement area (1d) comprises, on each side of the longitudinal central plane (Y2), an interdigital capacitive sensor (22d, 22'd) and a resistive electrode (12d, 12'd).

Clause 9. The seat according to clause 6, wherein:
the first measurement area (1a) comprises an interdigital capacitive sensor (23a) and a resistive electrode (13a) which are located substantially along a vertical central plane (Y1) of the backrest;
the second measurement area (1b) comprises, on each side of the vertical central plane (Y1), an interdigital capacitive sensor (23b, 23'b) and a resistive electrode (13b, 13'b);
the third measurement area (1c) comprises an interdigital capacitive sensor (23c) and a resistive electrode (13c) which are located substantially along a longitudinal central plane (Y2) of the seating portion; and
the fourth measurement area (1d) comprises, on each side of the longitudinal central plane (Y2), an interdigital capacitive sensor (23d, 23'd) and a resistive electrode (13d, 13'd).

Clause 10. The seat according to clause 6, wherein:
the first measurement area (1a) comprises an interdigital capacitive sensor (24a) and a resistive electrode (14a) which are located substantially along a vertical central plane (Y1) of the backrest;
the second measurement area (1b) comprises an interdigital capacitive sensor (24b) and a resistive electrode (14b) which are located substantially along the vertical central plane (Y1);
the third measurement area (1c) comprises, on each side of a longitudinal central plane (Y2) of the seating portion, an interdigital capacitive sensor (24c, 24'c) and a resistive electrode (14c, 14'c); and
the fourth measurement area (1d) comprises, on each side of the longitudinal central plane (Y2), an interdigital capacitive sensor (24d, 24'd) and a resistive electrode (14d, 14'd).

Clause 11. The seat according to clause 6, wherein:
the first measurement area (1a) comprises, on each side of a vertical central plane (Y1) of the backrest, an interdigital capacitive sensor (25a, 25'a) and a resistive electrode (15a, 15'a);
the second measurement area (1b) comprises, on each side of the vertical central plane (Y1), an interdigital capacitive sensor (25b, 25'b) and a resistive electrode (15b, 15'b), the second measurement area further comprising an interdigital capacitive sensor (25"b) and a resistive electrode (15"b) along the vertical central plane (Y1);
the third measurement area (1c) comprises, on each side of a longitudinal central plane (Y2) of the seating portion, an interdigital capacitive sensor (25c, 25'c) and a resistive electrode (15c, 15'c), the third measurement area further comprising an interdigital capacitive sensor (25"c) and a resistive electrode (15"c) along the longitudinal central plane (Y2); and
the fourth measurement area (1d) comprises, on each side of the longitudinal central plane (Y2), an interdigital capacitive sensor (24d, 24'd) and a resistive electrode (14d, 14'd).

Clause 12. The seat according to clauses 6 to 11, wherein at least one interdigital capacitive sensor is suitable for measuring a capacitance greater than 300 picofarads and less than 3500 picofarads, preferably less than 2500 picofarads if the at least one interdigital capacitive sensor is located in the second measurement area (1b) or in the fourth measurement area (1d); and wherein at least one resistive electrode is suitable for measuring a pressure of less than 300 g/cm², preferably less than 30 g/cm² if the resistive electrode is located in the first measurement area (1a), preferably greater than 30 g/cm² and less than 100 g/cm² if the resistive electrode is located in the second measurement area (1b), preferably greater than 65 g/cm² if the resistive electrode is located in the third measurement area (1c), preferably greater than 10 g/cm² and less than 50 g/cm² if the resistive electrode is located in the fourth measurement area (1d).

Clause 13. A controller (100) arranged so as to be connected to the at least one measurement area of a seat according to any one of the preceding claims, the controller being configured for determining a type of user occupying the seat, detecting the user, monitoring for lumbar pain of the user and/or monitoring for pelvic pain of the user.

Clause 14. The controller of clause 13, any other suitable clause, or combination of suitable clauses, the controller being an engine control unit which is external to the seat.

Clause 15. A measurement system comprising a seat according to one of clauses 1 to 12 and a controller according to one of clauses 13 to 14.

Clause 16. A measurement method implemented by means of a seat (1) comprising a backrest (10), a seating portion (20) connected to the backrest, at least one measurement area (1a, 1b, 1c, 1d) defined on the backrest and/or on the seating portion, the at least one measurement area comprising at least one interdigital capacitive sensor capable of measuring a distance or movement of a user occupying the seat, the at least one measurement area of the seat being connected to a controller (100) configured for determining a type of user occupying the seat or for detecting the user, the method comprising:

(S1) calibrating the at least one interdigital capacitive sensor by performing a measurement when the seat is not occupied;

(S2) determining, with the at least one calibrated interdigital capacitive sensor, a plurality of distances or movements of the user when the user is occupying the seat; and (S4) detecting the user or determining the type of user, based on a comparison between several of the determined distances or movements.

Clause 17. The measurement method of clause 16, wherein the at least one measurement area further comprises at least one resistive electrode capable of measuring a contact pressure of a user occupying the seat, the method further comprising:

(S2') determining, with the at least one calibrated resistive electrode, a plurality of contact pressures of the user; and (S3) fusing several of the determined contact pressures with several of the determined distances or movements, to form a set of fused measurements, the user detection or the user type determination being implemented based on a comparison between several of the fused measurements.

Clause 18. The measurement method of clause 16, wherein the controller (100) is further configured to monitor for lumbar pain of the user and/or pelvic pain of the user, the method further comprising:

(S4') monitoring for lumbar pain and/or pelvic pain of the user based on an average and/or a gradient of several of the determined distances or movements.

The invention claimed is:

1. A seat comprising:
a backrest;
a seating portion connected to the backrest; and
at least one measurement area defined on the backrest and/or on the seating portion, the at least one measurement area comprising at least one interdigital capacitive sensor capable of measuring a distance or a movement of a user occupying the seat,
wherein the seat comprises four measurement areas, the first and second of the measurement areas being formed on the backrest and one to each side of a horizontal central plane of the backrest, the third and fourth of the measurement areas being formed on the seating portion and one to each side of a transverse central plane of the seating portion and wherein:
the first measurement area comprises an interdigital capacitive sensor and a resistive electrode which are located on a same side of a vertical central plane of the backrest;
the second measurement area comprises an interdigital capacitive sensor and a resistive electrode which are located substantially along the vertical central plane;
the third measurement area comprises an interdigital capacitive sensor and a resistive electrode which are located substantially along a longitudinal central plane of the seating portion; and
the fourth measurement area comprises an interdigital capacitive sensor and a resistive electrode which are located on a same side of the longitudinal central plane.

2. The seat of claim 1, wherein the at least one measurement area further comprises at least one resistive electrode capable of measuring a contact pressure of a user occupying the seat.

3. The seat of claim 2, wherein the total number of interdigital capacitive sensors comprised in the seat is greater than one and less than six and wherein the total number of resistive electrodes comprised in the seat is greater than one and less than six.

4. The seat of claim 2, further comprising at least one measurement sheet forming the at least one measurement area and electrically connecting the at least one interdigital capacitive sensor to the at least one resistive electrode.

5. The seat of claim 4, wherein at least one distance separating the at least one interdigital capacitive sensor and the at least one resistive electrode is equal to about 20 millimeters.

6. The seat of claim 4, wherein at least one distance separating the at least one interdigital capacitive sensor and the at least one resistive electrode is less than about 50 millimeters and greater than about 10 millimeters.

7. The seat of claim 1, wherein at least one interdigital capacitive sensor is suitable for measuring a capacitance greater than about 300 picofarads and less than about 3500 picofarads if the at least one interdigital capacitive sensor is located in the second measurement area or in the fourth measurement area; and wherein at least one resistive electrode is suitable for measuring a pressure of less than about 300 g/cm² if the resistive electrode is located in the first measurement area greater than about 30 g/cm² and less than about 100 g/cm² if the resistive electrode is located in the second measurement area, greater than about 65 g/cm² if the resistive electrode is located in the third measurement area greater than about 10 g/cm² and less than about 50 g/cm² if the resistive electrode is located in the fourth measurement area.

8. The seat of claim 1, wherein at least one interdigital capacitive sensor is suitable for measuring a capacitance greater than about 300 picofarads and less than about 2500 picofarads if the at least one interdigital capacitive sensor is located in the second measurement area or in the fourth measurement area; and wherein at least one resistive electrode is suitable for measuring a pressure of less than about 30 g/cm2 if the resistive electrode is located in the first measurement area, greater than about 30 g/cm2 and less than about 100 g/cm2 if the resistive electrode is located in the second measurement area, greater than about 65 g/cm2 if the resistive electrode is located in the third measurement area, greater than about 10 g/cm2 and less than about 50 g/cm2 if the resistive electrode is located in the fourth measurement area.

9. A seat comprising:
a backrest;
a seating portion connected to the backrest; and
at least one measurement area defined on the backrest and/or on the seating portion, the at least one measurement area comprising at least one interdigital capacitive sensor capable of measuring a distance or a movement of a user occupying the seat,
wherein the seat comprises four measurement areas, the first and second of the measurement areas being formed on the backrest and one to each side of a horizontal central plane of the backrest, the third and fourth of the measurement areas being formed on the seating portion and one to each side of a transverse central plane of the seating portion and wherein:
the first measurement area comprises, on each side of a vertical central plane of the backrest, an interdigital capacitive sensor and a resistive electrode;
the second measurement area comprises an interdigital capacitive sensor and a resistive electrode which are located substantially along the vertical central plane;
the third measurement area comprises an interdigital capacitive sensor and a resistive electrode which are located substantially along a longitudinal central plane of the seating portion; and
the fourth measurement area comprises, on each side of the longitudinal central plane, an interdigital capacitive sensor and a resistive electrode.

10. A seat comprising:
a backrest;
a seating portion connected to the backrest; and
at least one measurement area defined on the backrest and/or on the seating portion, the at least one measurement area comprising at least one interdigital capacitive sensor capable of measuring a distance or a movement of a user occupying the seat,
wherein the seat comprises four measurement areas, the first and second of the measurement areas being formed on the backrest and one to each side of a horizontal central plane of the backrest, the third and fourth of the measurement areas being formed on the seating portion and one to each side of a transverse central plane of the seating portion and wherein:
the first measurement area comprises, on each side of a vertical central plane of the backrest, an interdigital capacitive sensor and a resistive electrode;
the second measurement area comprises, on each side of the vertical central plane, an interdigital capacitive sensor and a resistive electrode, the second measurement area further comprising an interdigital capacitive sensor and a resistive electrode along the vertical central plane;
the third measurement area comprises, on each side of a longitudinal central plane of the seating portion, an interdigital capacitive sensor and a resistive electrode, the third measurement area further comprising an interdigital capacitive sensor and a resistive electrode along the longitudinal central plane; and
the fourth measurement area comprises, on each side of the longitudinal central plane, an interdigital capacitive sensor and a resistive electrode.

* * * * *